US011213497B2

(12) United States Patent
Koppisch et al.

(10) Patent No.: US 11,213,497 B2
(45) Date of Patent: Jan. 4, 2022

(54) ANTIBIOFILM FORMULATIONS

(71) Applicants: ARIZONA BOARD OF REGENTS ON BEHALF OF NORTHERN ARIZONA UNIVERSITY, Phoenix, AZ (US); DIXIE STATE UNIVERSITY, St. George, UT (US); TRIAD NATIONAL SECURITY, LLC, Los Alamos, NM (US); COLLEGE OF NEW JERSEY, Ewing, NJ (US)

(72) Inventors: Andrew T. Koppisch, Flagstaff, AZ (US); Gerrick E. Lindberg, Flagstaff, AZ (US); David T. Fox, Los Alamos, NM (US); Joseph Baker, Ewing, NJ (US); Alexanndra J. Heyert, Flagstaff, AZ (US); Rico Del Sesto, St. George, UT (US); Joshua R. Greene, Flagstaff, AZ (US)

(73) Assignees: ARIZONA BOARD OF REGENTS ON BEHALF OF NORTHERN ARIZONA UNIVERSITY, Flagstaff, AZ (US); TRIAD NATIONAL SECURITY, LLC, Los Alamos, NM (US); DIXIE STATE UNIVERSITY, St. George, UT (US); THE COLLEGE OF NEW JERSEY, Ewing, NJ (US)

(*) Notice: Subject to any disclaimer, the term of this patent is extended or adjusted under 35 U.S.C. 154(b) by 0 days.

(21) Appl. No.: 16/307,347

(22) PCT Filed: May 31, 2018

(86) PCT No.: PCT/US2018/035475
§ 371 (c)(1),
(2) Date: Dec. 5, 2018

(87) PCT Pub. No.: WO2018/222924
PCT Pub. Date: Dec. 6, 2018

(65) Prior Publication Data
US 2020/0323799 A1 Oct. 15, 2020

Related U.S. Application Data

(60) Provisional application No. 62/513,983, filed on Jun. 1, 2017.

(51) Int. Cl.
| | | |
|---|---|---|
| *A61K 31/14* | (2006.01) |
| *A01N 27/00* | (2006.01) |
| *A01N 37/00* | (2006.01) |
| *A61K 31/01* | (2006.01) |
| *A61K 31/11* | (2006.01) |
| *A61K 31/20* | (2006.01) |

(52) U.S. Cl.
CPC .............. *A61K 31/14* (2013.01); *A01N 27/00* (2013.01); *A01N 37/00* (2013.01); *A61K 31/01* (2013.01); *A61K 31/11* (2013.01); *A61K 31/20* (2013.01)

(58) Field of Classification Search
CPC ........ A61K 31/14; A61K 31/11; A61K 31/20; A61K 31/01; A61K 2300/00; A01N 37/00; A01N 27/00
See application file for complete search history.

(56) References Cited

U.S. PATENT DOCUMENTS

| 9,278,134 B2 | 3/2016 | Rogers et al. | |
| 2006/0166856 A1 | 7/2006 | Petrat et al. | |
| 2013/0252945 A1* | 9/2013 | Lovejoy ................. | A01N 59/16 514/217 |
| 2014/0274713 A1 | 9/2014 | Barrientos et al. | |
| 2015/0335549 A1* | 11/2015 | Patel ....................... | A61K 31/14 424/401 |
| 2016/0312155 A1 | 10/2016 | Sutton et al. | |
| 2018/0093011 A1 | 4/2018 | Kellar et al. | |

* cited by examiner

*Primary Examiner* — Yanzhi Zhang
(74) *Attorney, Agent, or Firm* — Knobbe, Martens, Olson & Bear LLP

(57) ABSTRACT

Methods and compositions related to molecules and formulations comprising antibiofilm materials are provide, including new formulations of Deep Eutectic Solvents (DES) that are chemically related to choline geranate. Specifically, geranic acid (a component of choline geranate DES) is a molecule from the isoprenoid/terpene family of compounds. Other members of this family as DES components include isoprenoid acids and chemical derivatives thereof.

17 Claims, 14 Drawing Sheets

ANTIBIOFILM FORMULATIONS

INCORPORATION BY REFERENCE TO RELATED APPLICATIONS

Any and all priority claims identified in the Application Data Sheet, or any correction thereto, are hereby incorporated by reference under 37 CFR 1.57. This application is the national phase under 35 U.S.C. § 371 of prior PCT International Application No. PCT/US2018/035475 which has an International Filing Date of May 31, 2018, which designates the United States of America, and which claims priority to U.S. Provisional Application No. 62/513,983 filed Jun. 1, 2017. Each of the aforementioned applications is incorporated by reference herein in its entirety, and each is hereby expressly made a part of this specification.

GOVERNMENT FUNDING

This invention was made with Government support under grant numbers CHE-1412628, ACI-1550562, and ACI-1550528 funded by the National Science Foundation. The Government has certain rights in the invention.

FIELD

Methods and compositions related to molecules and formulations comprising antibiofilm materials are provide, including new formulations of Deep Eutectic Systems (DES, sometimes referred to as deep eutectic solvents, eutectic mixtures, or binary mixtures) that are chemically related to choline geranate. The compositions are also contemplated for use in surface decontamination. Specifically, geranic acid (a component of choline geranate DES) is a molecule from the isoprenoid/terpene family of compounds. Other members of this family as DES components include isoprenoid acids, chemical derivatives of isoprenoid acids, or neutral species that themselves solvate in liquid solutions of isoprenoid compound based ionic liquids. Also contemplated are DES of different isoprenoid acid composition, as well as 1:1 choline geranate (CAGE) with other neutral species that behave as geranic acid and use of a 1:1 CAGE as a delivery vehicle for antibiofilm drugs.

SUMMARY

The present disclosure relates to formulations for disruption of biofilms.

Accordingly, in some embodiments is provided an ionic liquid matrix comprising a neutral species, an isoprenoid anion and a cholinium cation. In some embodiments, the neutral species, the isoprenoid anion, and the cholinium cation are present in a molar ratio of 1:1:1.

In some embodiments, the neutral species the neutral species is selected from the group consisting of an isoprenoid acid, isoprenoid alcohol, isoprenoid hydrocarbon, phenylpropanoid, fatty acid, and terpenoid alcohol.

In some embodiments, the neutral species is an isoprenoid acid selected from the group consisting of geranic acid, citronellic acid, cinnamic acid, vanillic acid, gibberelic acid, isovaleric acid, abscisic acid, indole-3-butyric acid, a cholic acid derivative, a benzoic acid derivative, and a salicylic acid derivative.

In some embodiments, the neutral species is an isoprenoid alcohol selected from the group consisting of farnesol, geraniol, citronellol, nerol, R/L-linalool, R/L-lavandulol, geranylgeraniol, cis/trans nerolidol, retinol, β-rhodinol, and acylated myrcene.

In some embodiments, the neutral species is a terpenoid alcohol selected from the group consisting of carvacrol, (−)/(+)/cis/trans carveol, thymol, α-/β/γ-terpeniol, terpini-4-ol, D/L-menthol, (−)/(+)-isoborneol, eucalyptol, guaiol, (−)/(+)-bisabolol, borneol, prenol, isoprenol, humulone, isohumulone, α-/β/δ/γ-tocopherol, camphor, menthone, verbenone, citral, citronaldehyde, geranial, geranyl acetate, lavandulal actate, linalool acetate, pulegone, zingerone and carvone.

In some embodiments, the neutral species is an isoprenoid hydrocarbon selected from the group consisting of D/L-limonene, α/β-pinene, α/β-farnesene, α/β-carotene, cedrene, camphene, p-cymene, myrcene, ocimene, sabinene, terpinolene, bergamotene, phellandrene, squalene, squalane, α/β-humulene, and a vitamin K derivative.

In some embodiments, the neutral species is a phenylpropanoid selected from the group consisting of cinnamaldehyde, cinnamyl alcohol, cinnamilic acid, vanillin, vanillyl alcohol, vanillic acid, benzaldehyde, methylchavicol, eugenol, capsaicin, curcumin, salicylic acid, and protocatechuic acid.

In some embodiments, the isoprenoid anion is selected from the group consisting of geranate anion, citronellate anion, cinnamate anion, gibberelate anion, isovalerate anion, absciscate anion, indole-3-butyrate anion, salicylate anion, protocatechuate anion and abietate anion.

In some embodiments is provided an antibiofilm material comprising the ionic liquid matrix as described above and a solvent.

In some embodiments, the antibiofilm material comprises an ionic liquid matrix present in the antibiofilm material at a concentration of from 0.01% by volume to 20% by volume. In some embodiments, the ionic liquid matrix is present in the antibiofilm material at a concentration of from 0.1% by volume to 15% by volume. In some embodiments, the ionic liquid matrix is present in the antibiofilm material at a concentration of from 1% by volume to 10% by volume.

In some embodiments, the antibiofilm material further comprises a compound exhibiting stabilizing or preservative activity. In some embodiments, the compound exhibiting stabilizing or preservative activity is selected from the group consisting of α-tocopherol, α-tocopherol acetate, β-carotene, lutein, salicylic acid, protocatechuic acid. In some embodiments, the compound exhibiting stabilizing or preservative activity is present at a concentration of 0.1% by volume to 5% by volume. In some embodiments, the compound exhibiting stabilizing or preservative activity is present at a concentration of 1% by volume to 2% by volume.

In some embodiments is provided a method of killing a bacterium comprising contacting a bacterium with the antibiofilm material described above and killing the bacterium. In some embodiments, the bacterium is from the group consisting of *Staphylococcus aureus, Pseudomonas aeruginosa, Enterobacter cloacae, Enterococcus* sp., *Escherichia coli, Acinetobacter baumani*, and *Klebsiella pneumoniae*.

In some embodiments, the antibiofilm material is used as a cleaning solution. In some embodiments, the antibiofilm is used as a delivery vehicle for a drug.

DETAILED DESCRIPTION

Figure 1:
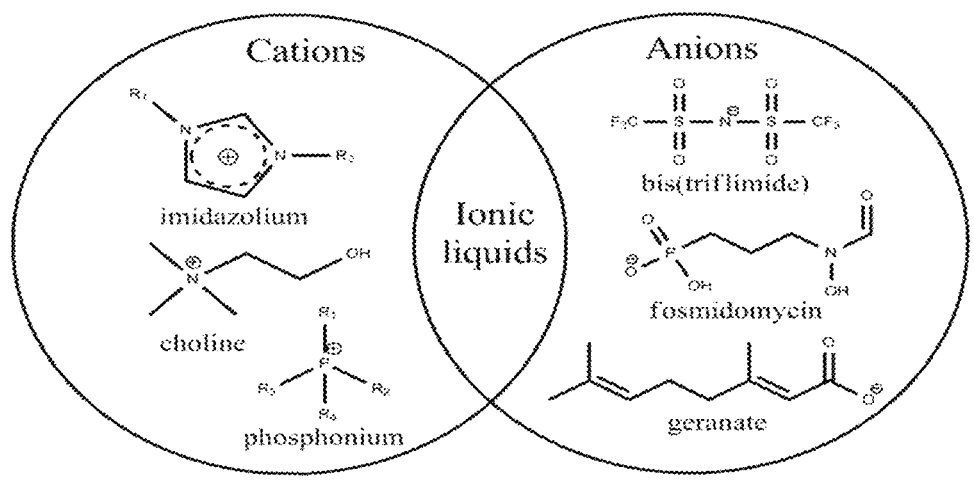
FIG. 1 depicts ILs/DESs, which are a family of molten salts comprised of an organic cation with either an organic or inorganic anion.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Definitions

The term "ionic liquid" as used herein is a broad term, and is to be given its ordinary and customary meaning to a person of ordinary skill in the art (and is not to be limited to a special or customized meaning), and refers without limitation to a material that is liquid at working temperatures and comprised of one organic or inorganic cation and one organic or inorganic ion (e.g., binary, ternary, or higher order ions).

The term "eutectic system" as used herein is a broad term, and is to be given its ordinary and customary meaning to a person of ordinary skill in the art (and is not to be limited to a special or customized meaning), and refers without limitation to a mixture of two or more substances which when combined yield a separately identifiable material.

The term "deep eutectic system" as used herein is a broad term, and is to be given its ordinary and customary meaning to a person of ordinary skill in the art (and is not to be limited to a special or customized meaning), and refers without limitation to a material that engages in primary acid-base-hydrogen transfer/bonding interactions between the molecules from which it is comprised, which can also include ions.

The term "binary mixture" as used herein is a broad term, and is to be given its ordinary and customary meaning to a person of ordinary skill in the art (and is not to be limited to a special or customized meaning), and refers without limitation to a mixture of two materials that have new properties (e.g., eutectics, azeotropes, etc.) compared to the properties of the individual materials.

Alcohols, fatty acids, alkyl acids, and aldehydes in a 1:1 ionic liquid matrix, such as choline geranate can be deep eutectic systems based on their ability to form hydrogen bonds. These combinations can be more generally described as eutectic systems. Hydrocarbons in 1:1 CAGE can be described as a eutectic system for those hydrocarbons that do not phase separate and for which the melting point is lower than 1:1 CAGE. A mixture of a hydrocarbon in a 1:1 CAGE, wherein the hydrocarbon is capable of evaporating from the mixture, can be considered as binary mixtures. Each of these three mixture types (deep eutectic systems, eutectic systems, and binary mixtures) can be advantageously employed in the various embodiments to yield antibiofilm formulations.

Antibiofilm Liquids

Many isoprenoid acids, such as citronellic acid or nerolic acid, are generally regarded as safe by the Flavor and Extract Manufacturers Association (FEMA). Isoprenoids/terpenes are the primary components of what are termed "essential oils" of plants. Essential oils, however, are considered by the field of flavorings to be those that are primarily hydrocarbons (such as limonene, pinene, etc.) or isoprenoid alcohols (geraniol, farnesol, etc.), and are not typically considered for use as biofilms. Other metabolites in essential oils (such as the phenylpropanoid cinnemaldehyde) have been utilized as antibacterial agents; however, they cannot be formulated into an ionic liquid, and they are generally insoluble in water.

Antibiofilm ionic liquids and deep eutectic solvents are capable of disrupting biofilms of pathogenic bacteria and of crossing the skin to do so. Some antibiofilm ionic liquids and deep eutectic solvents, such as CAGE, are also able to kill microbial cells within the biofilm after it has been disrupted. Terpene metabolites may be able to have a degree of antibacterial activity or ability to pass into dermis (such as the alpha-tocopherols that comprise vitamin E are commonly included in skin creams); however, both antibacterial and skin penetrating ability have not been reported.

Computational modeling approaches and cell viability assays have provided mechanistic insight into molecular features of the materials (such as CAGE), and the ingredients within the biofilm disrupting composite materials, which aid antibacterial activity. Given this information, new molecular formulations with comparable biological activity may be designed.

Biologically active DES can involve a) a protonated hydrocarbon acid, b) the anion of the aforementioned acid, and c) a cation (e.g., those that are derived from a protonated or otherwise positively charged amine based molecules). Specifically, one effective formulation is a DES composed of molar equivalents of a) geranic acid, b) geranate anion, and c) cholinium cation.

Other hydrocarbon acid/hydrocarbon anion compositions may similarly result in efficacious formulations. Data suggests that the inclusion of an acidic neutral species (e.g., hydrocarbon acid, fatty acid) is particularly important for full saturation of both leaflets of a representative bacterial cell membrane, which in turn is key to rendering the cell possessing the membrane inviable. Formulations of 1:1 equimolar pairings of choline and geranate anion—a true ionic liquid (IL)—have not been observed to be as effective as antibacterial agents as DES formulations of the same material (e.g., those that are comprised of 1:1:1 equimolar pairings of choline, geranate anion, and geranic acid).

Of particular interest are new deep eutectic systems, eutectic systems, or binary systems that incorporate isoprenoid acids (geranic acid is an isoprenoid acid) such as citronellic acid, nerolic acid, other naturally occurring isoprenoid acids, or chemical derivatives of these groups, such as saturated or saturated and unbranched hydrocarbon derivatives. Numerous isoprenoid acids are already regarded as safe by the FEMA. In addition to geranate ions, other ions or ion sources suitable for use include but are not limited to citronellate, cinnamate, gibberelate, abietate, and others that act in a similar manner to geranate.

While 1:1 equimolar pairings can advantageously be employed in an antibiofilm, 2:1 deep eutectic system formulations can also be employed. Data further indicates that the nature of the neutral species may be changed as well, and may similarly potentiate the antibiofilm/antibacterial properties relative to the 1:1 mixture, or minimally does not elicit a marked loss of antibiofilm/antibacterial properties. For example, formulations that include the following neutral species are envisioned: protonated acids (e.g., isoprenoid acids), isoprenoid alcohols, and isoprenoid hydrocarbons. In addition to isoprenoids, other bioactive components can be included as well, e.g., phenylpropanoids (shikimate metabolites) or fatty acids. Formulations with protonated acids include 1:1 CAGE with citronellic acid or 1:1 choline citronellate (CACI) with geranic acid or citronellic acid. A CAGE or CACI scaffold can be provided with other acids, such as cinnamic acid, vanillic acid, gibberelic acid, derivatives of benzoic acid, or derivatives of salicylic acid. Other isoprenoid acids include absciscic acid, artesunate, carnosic acid, chenodeoxycholic acid, cholic acid, +/−chrysanthemic acid, deoxycholic acid, fusidic acid, glycocholic acid, isosteviol, isopimaric acid, isovaleric acid, phytanic acid, pristanic acid, steviol, tetrahydrocannabinic acid, cannabigerolic acid, Δ9 tetrahydrocanabinolic acid, cannabidiolic acid, cannabidiolic acid, cannabichromenenic acid, cannabigerovarinic acid, tetrahydrocannabivaric acid, cannabidivarinic acid, cannabichromevarinic acid, and ursolic acid.

Additionally, it is envisioned that other compounds may be used which include amcinonide, artemesin, artemether, artemotil, butamethasone, camphor, chrysanthone, citral, citronaldehyde, clobetasol propionate, clobetasone, cortisone, cortisol, cuminaldehyde, desonide, drospiranone, ethinyl estradiol, farnesyl acetate, fenchone, flucloronide, fludocortisone, fludroxycortide, fluocinolone acetonide, fluticasone, formocortal, halcinonide, halometasone, hydrocortisone, geranal acetate, geranial, geranylgeranyl acetone (teprenone), indometacin farnesil, α,β,γ-ionone, lavandulal acetate, linalool acetate, loteprednol, menthofuran, methone, methyl acetate, mometasone furoate, neral, nootkatone, R/S-perillyl aldehyde, perilla ketone, piperitone, prenamustine, prednisone, premarin, pulegone, +/−rose oxide, safranal, salvinorins A-J, trans-sorbrerol, synthetic progestogens, progestin, α/β-thujone, tocopherol acetate, triamcinolone acetonide, +/−verbenone, vetiver acetate, whiskey lactone, wine lactone, and zingerone.

Isoprenoid Alcohols

The following are representative examples of members of a family of molecules known as acyclic terpenoid alcohols. They are found in natural sources such as essential oils. Many of these exist with common isomeric forms (R/S, D/L or +/−). These alcohols can be employed in the formulations of the embodiments. Geraniol, citronellol, nerol and acylated myrcene (all extremely chemically similar) all have a very low toxicity/mutagenicity potential. Farnesol and linalool are known to be microbial signaling molecules, and geraniol is similarly bioactive. Furthermore, linear alcohols such as dolichol, geranylgeraniol, isophytol, cis/trans-nerolidol, retinol, and β-rhodinol may be suitable.

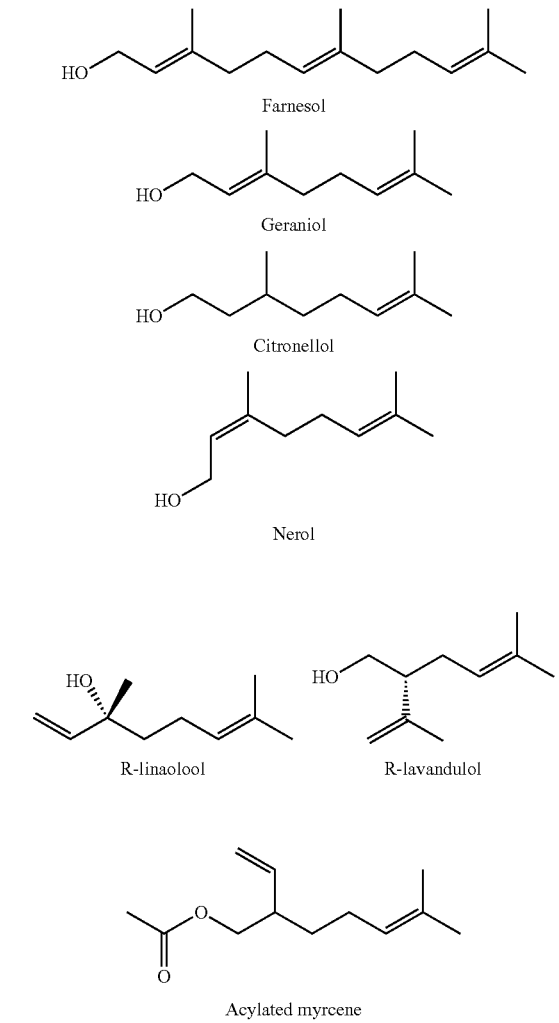

The following are a representative selection of common cyclized terpenoid alcohols abundant in nature. These are similarly abundant in nature and already found in many commercial disinfectants, mouthwash, topical creams/lotions, and the like.

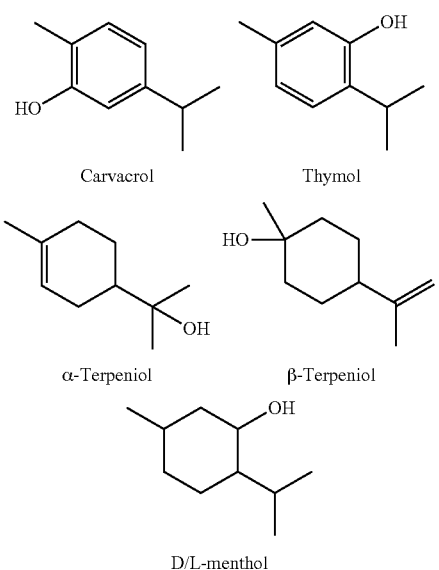

Carvacrol  Thymol

α-Terpeniol  β-Terpeniol

D/L-menthol

Common terpenoid alcohols with varied structures are provided below. They are also components of other commercial products. Camphor (oxidized isoborneol) and eucalyptol are common cough suppressants (e.g., Vicks Vap-o-rub and similar products). Humulone and isohumulone are bittering agents in beer, and also exhibit antibiofilm abilities. Carvone is an oxidized terpenoid alcohol found in black pepper. Additional examples of suitable cyclic alcohols include andrographolide, aphidicolin, α/β-bisabolol, α/β-cadinol, cafestol, capsidiol, carotol, +/−cis/trans-carveol, carnosol, cedrol, cholicalciferol, docetaxel, ergocalciferol, estradiol and associated derivatives, feruginol, +/−fenchyl alcohol, ginkolides, guaiol, hinokitiol, ingenol mebutate, isoprenol, patchoulol, R/S perillyl alcohol, prenol, α/β-santalol, scleriol, testosterone and associated derivatives, tetrahydrocannabinol, α,β,γ-terpneol, terpine-4-ol, thioterpineol, thymol, α,β,δ,γ-tocopherol, verbenol, zeaxnthin, cannabigerol, tetrahydrocannabinol, cannabidiol, cannabichromene, cannabigerviarin, tetrahydrocannabivarin, cannabidivarin, and cannabichromevarin.

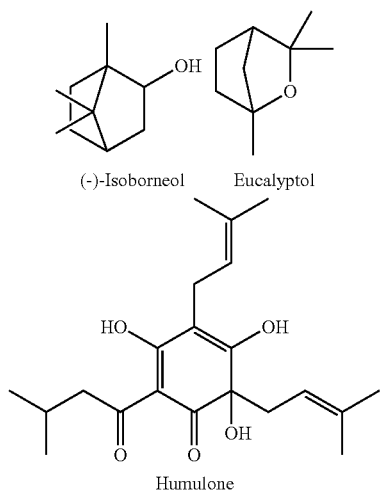

(-)-Isoborneol  Eucalyptol

Humulone

-continued

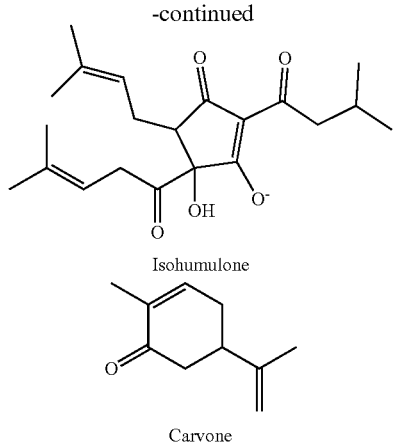

Isohumulone

Carvone

Representative examples of isoprenoid hydrocarbons are provided below. Many of these are common additives in surface cleaners/disinfectants/sterilizers. Inclusion of these compounds in formulations of the embodiments can yield similar cleaning agents that can similarly break down into environmentally innocuous materials, e.g., for use as green cleaners for household use. Other hydrocarbons include bornane, cadalene, camphene, carinene, α-carotene, δ-carotene, cedrene, p-cymene, α,β,γ-guaiene, guaiazulene, humulene, isoprene, norbornane, ocimene, phellandrene, phytane, phytoene, sabinene, aqualene, squalene, terpinolene, terpinene, α/β-thujene, valencene, Vitamin K1, Vitamin K2 (MK-4), and Vitamin K2 (MK-7).

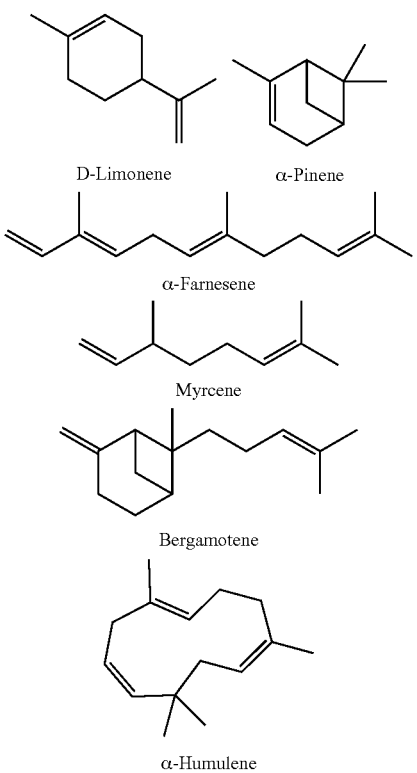

D-Limonene  α-Pinene

α-Farnesene

Myrcene

Bergamotene

α-Humulene

Representative examples of phenylpropanoids include the following. Many bioactive molecules are derived from shikimate pathway metabolites as opposed to isoprenoids, and often possess antibacterial/antibiofilm abilities. The aldehydes below are found in essential oils and used commonly as flavorings, and alcohol and acid derivatives readily exist.

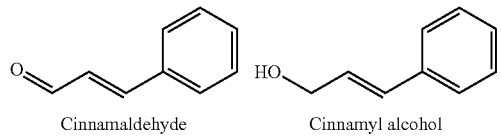

Cinnamaldehyde    Cinnamyl alcohol

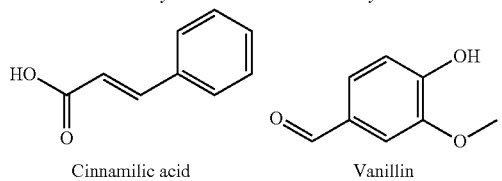

Cinnamilic acid    Vanillin

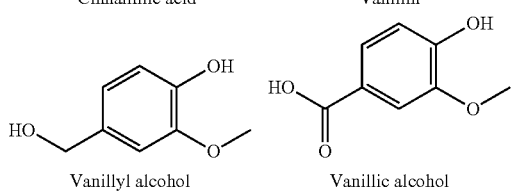

Vanillyl alcohol    Vanillic alcohol

Other examples of phenylpropanoids include the following compounds.

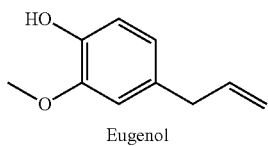

Eugenol

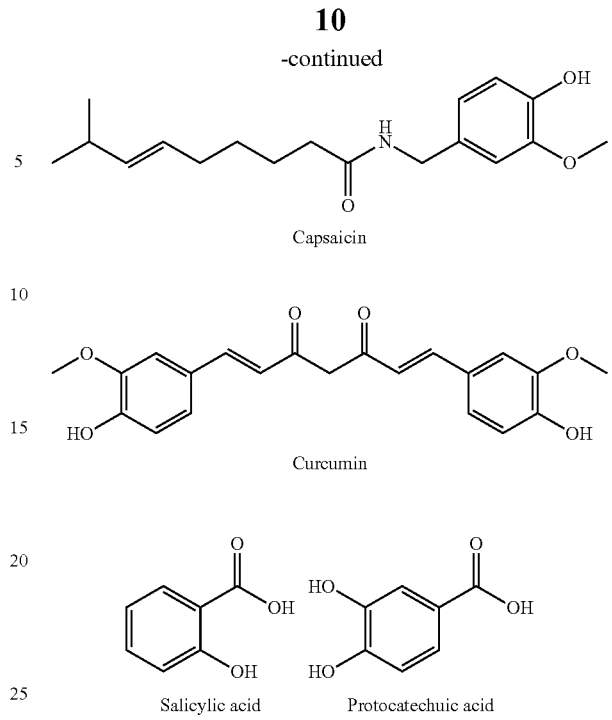

Capsaicin

Curcumin

Salicylic acid    Protocatechuic acid

Other compounds exhibiting stabilizing and preservative activity can be included in the antibiofilm formulations of the embodiments. These molecules include natural antioxidants and/or common preservatives such as vitamin E, tocopherol acetate, and the carotenoids, which are common vitamin nutraceuticals. Vitamin E and tocopherol acetate are also part of many cosmetics/skin lotions. Representative examples include the following.

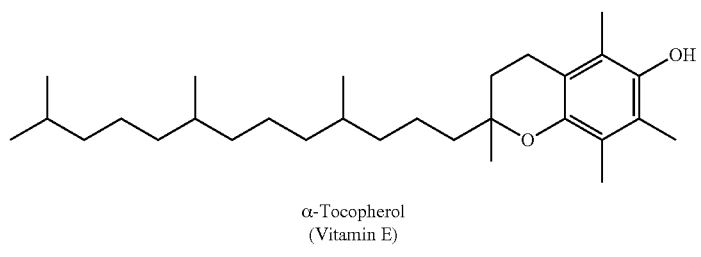

α-Tocopherol
(Vitamin E)

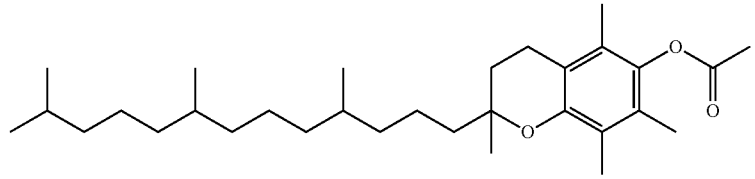

α-Tocopherol
acetate

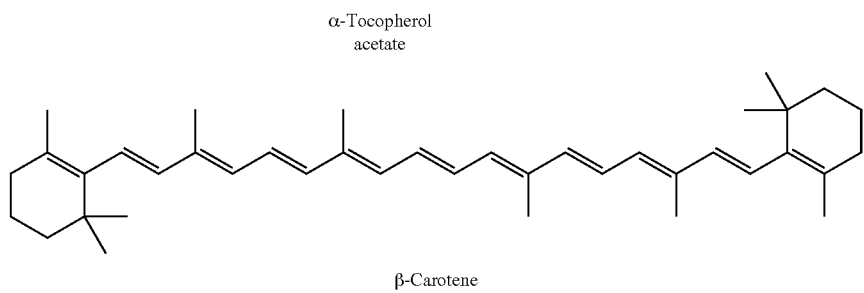

β-Carotene

-continued

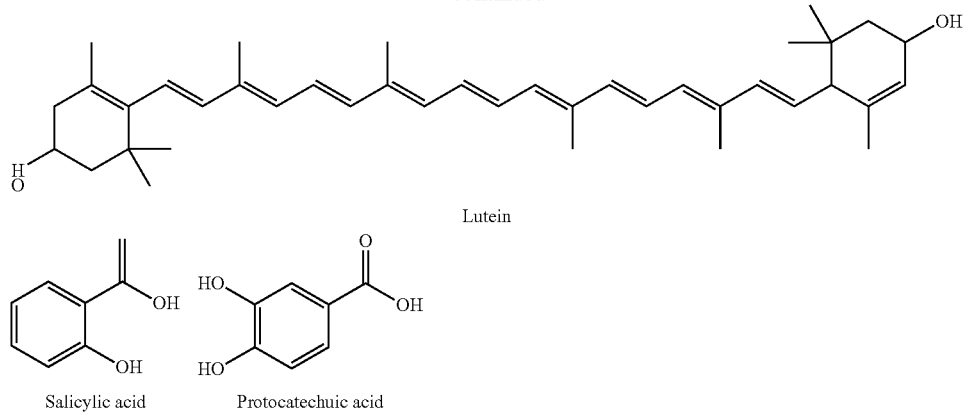

Lutein

Salicylic acid    Protocatechuic acid

Such stabilizers and preservatives can be included in a deep eutectic system, a eutectic system, or a binary system. When included, they can be used in any suitable concentration, e.g., 0.1% or less to 5% or more by volume, e.g., 1% to 2% by volume. In certain embodiments, such compounds can be present in equal portions to a 1:1 CAGE in order to make a 2:1 DES.

Molecular Modeling

Molecular modeling was done with the use of computational resources/servers. Antibiofilm experiments and chemical characterization methods (e.g., NMR) were performed in research labs/equipment labs. Novel deep eutectic solvents (e.g., choline citronellate) were obtained for screening.

It was shown that most ESKAPE pathogens show MBEC values between 0.3 and 1.25% CAGE. Time-kill assays demonstrate greater than 99% reduction in biofilm viability within 30 minutes with 0.1% CAGE challenged against a mature biofilm of Staphylococcus aureus. SEM images show tears/destruction of biofilm begin within 5 minutes. Molecular modelling suggests that bacterial cells are effected by overpopulation of membranes with CAGE. Studies regarding CAGE stability will be performed and testing of CAGE and CAGE analogues will continue against more ESKAPE pathogens.

Utilization of Ionic Liquids for Pathogen Neutralization

Due to recent FDA mandates, there is a need for new antiseptic agents for use in the clinical setting that are considered Generally Regarded as Safe (GRAS). FDA has effectively ruled most antiseptics that are currently in use are no longer GRAS, and may not be marketed industrially for much longer. Multiple ionic liquids (ILs) and deep eutectic solvents (DESs) and identified one particular deep eutectic solvent, choline geranate (CAGE), were tested that both exhibited potent anti-bacterial properties as well as being generally non-toxic to mammalian skin cell lines. Antiseptic agents are a critical tool to combat the spread of infections. These antimicrobial compounds are used in the healthcare industry to sterilize surfaces and synthetic substrates, and also to cleanse skin prior to surgical action or to flush wounds. Currently, the FDA recognizes 29 antiseptic ingredients. While the use of antiseptics in society is widespread, an FDA review in May of 2015 has called into question the safety and efficacy of ingredients within many commonly used products. Consequently, there is a need for new antiseptic agents that are generally regarded as safe (GRAS).

The use of ionic liquids (ILs) and deep eutectic solvents (DESs) as new antiseptic agents has been investigated. ILs/DESs are a family of molten salts comprised of an organic cation with either an organic or inorganic anion, as shown in FIG. 1.

Figure 2:
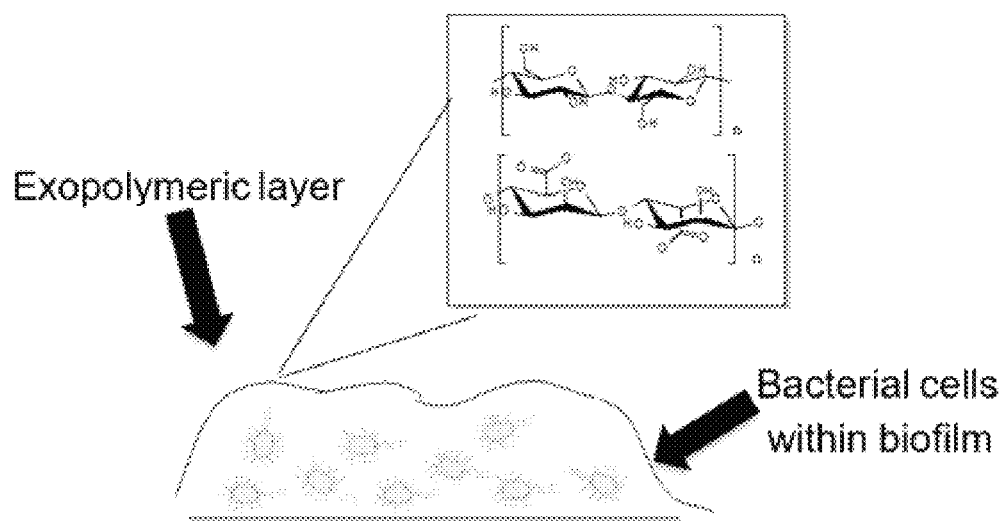
FIG. 2 depicts how ILs/DESs are known to be capable of disrupting the hydrogen bonding networks within recalcitrant biopolymers, of which the exopolymeric layer that protects bacterial biofilms is comprised.

Many ILs/DESs are known to be capable of disrupting the hydrogen bonding networks within recalcitrant biopolymers, of which the exopolymeric layer that protects bacterial biofilms is comprised, as shown in FIG. 2.

Figure 3A:
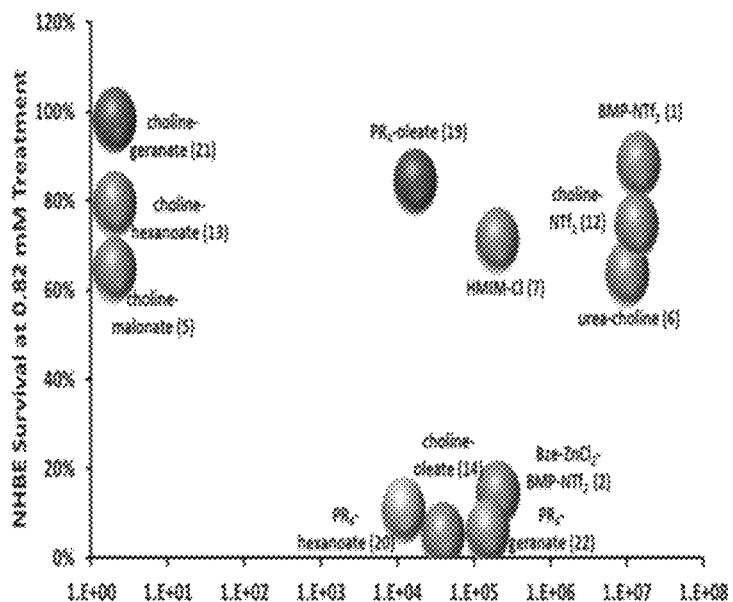
FIG. 3A shows the correlation of IL/DES cytotoxicity effects on normal human bronchial epithelial (NHBE) cells and antibiofilm activity on S. enterica.
Figure 3B:
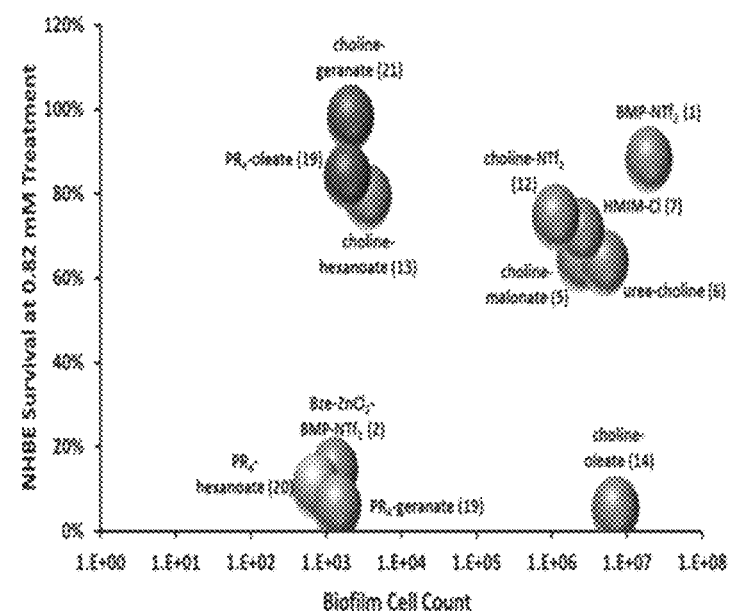
FIG. 3B shows the correlation of IL/DES cytotoxicity effects on normal human bronchial epithelial (NHBE) cells and antibiofilm activity on P. aeruginosa.

Biofilms are responsible for up to 65-80% of all bacterial infections in humans and are ~50-1000 times less sensitive to antimicrobials than their planktonic counterparts. One particular DES, choline geranate exhibited potent antimicrobial properties and was generally non-toxic to mammalian skin cell lines. CAGE showed broad-spectrum activity against a panel of bacteria relevant to human disease, including numerous MDR isolates. CAGE is able to pass through the dermal layers to treat bacterial infections within the skin which is particularly salient given the deleterious effects of biofilm-mediated infections in wound healing. The correlation of IL/DES cytotoxicity effects on normal human bronchial epithelial (NHBE) cells and antibiofilm activity on S. enterica (FIG. 3A) and P. aeruginosa (FIG. 3B) is discussed in Zakrewsky M, et al. (2014) Ionic liquids as a class of materials for transdermal delivery and pathogen neutralization. Proc Natl Acad Sci USA 111(37): 13313-13318.

The efficacy of CAGE against mature biofilms of clinically isolated ESKAPE pathogens has been tested using minimum biofilm eradication concentration (MBEC) and time-kill assays. Results indicate that CAGE retains its antibacterial efficacy upon aqueous dilution and at relatively short exposure times. Time-kill assays on early (24 hr) and mature (72 hr) biofilms of Staphyococcus aureus (MSSA) indicate that 0.1% CAGE in water compares to 10% bleach in terms of antiseptic action. The mechanism of biofilm disruption and eradication via scanning election microscopy (SEM) imaging and molecular modeling studies is being investigated.

The following are structures of geranate and choline, respectively (CAGE (IL)):

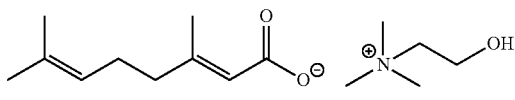

A 2:1 ratio provides CAGE (DES), as shown in the following figure:

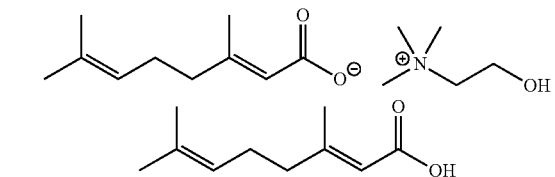

CAGE DES is synthesized via a salt metathesis reaction wherein two molar equivalents of geranic acid are mixed with one equivalent of choline bicarbonate as neat reagents. Upon completion of the reaction excess water is removed in vacuo (60° C.; 16 hrs) and the DES is stored at RT under $N_2$.

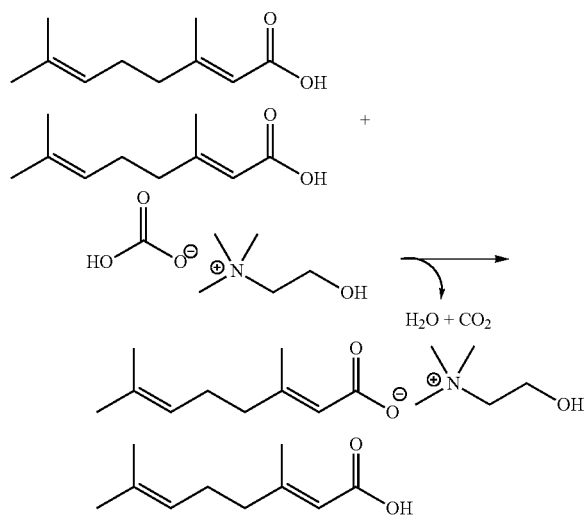

Figure 4:
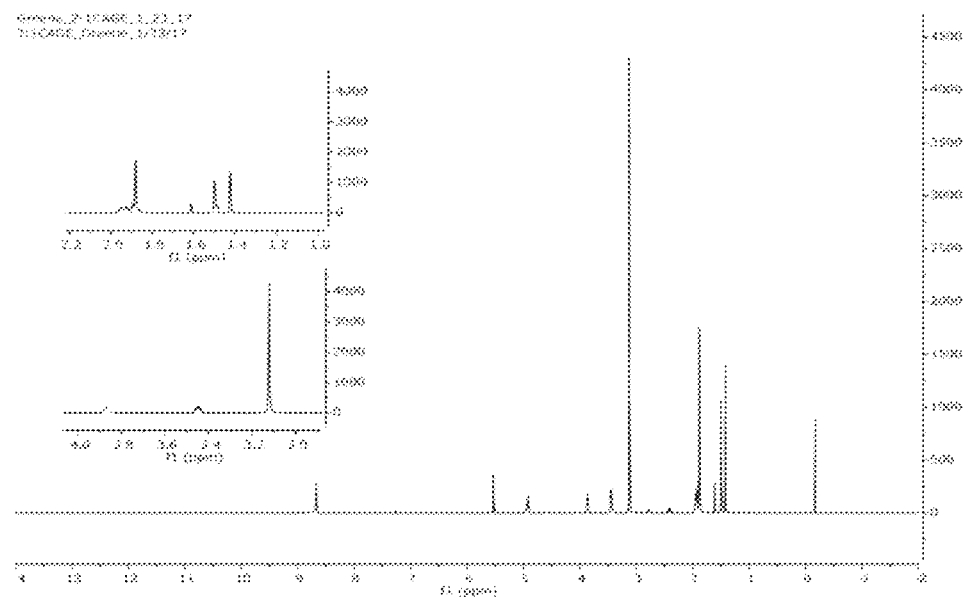
FIG. 4 shows the $^1$H NMR spectrum of CAGE.

The $^1$H NMR spectrum of CAGE is provided in FIG. 4.

Figure 5:
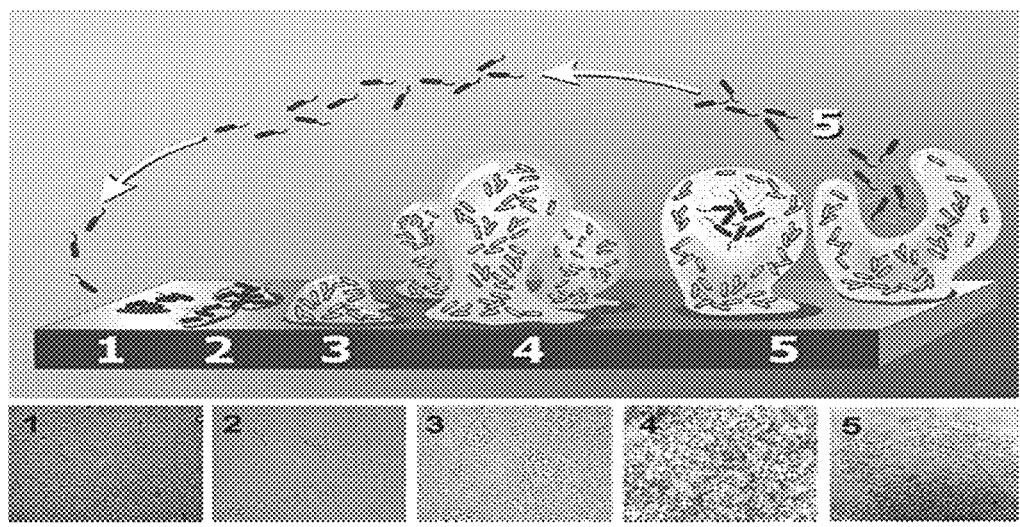
FIG. 5 shows a generalized transgression of biofilm formation on a solid surface.

Biofilms formed from bacteria are composed of a structurally complex extracellular polysaccharide matrix as a protection mechanism for the microbe. Biofilm-protected microorganisms are thought to be responsible for up to 65-80% of all bacterial infections in humans and are typically 50-1000 times less sensitive to antimicrobials than unprotected (planktonic) bacteria. It has been shown that CAGE is an effective antimicrobial against several of the ESKAPE pathogens, and the SEM images obtained demonstrate that CAGE effectively disrupts biofilms. The mechanism by which CAGE acts as an antimicrobial has been investigated via molecular modelling, and it appears that the mode of action is via saturation of the outer and inner leaflets of the plasma membrane; this mode of action was previously unknown to the field as current knowledge teaches that cell neutralization occurs by overloading the outer membrane with the alkyl anion, causing the cell to burst. As this common understanding of cell neutralization does not apply to the inventive compositions described herein, the present invention provides novel DES compositions not anticipated by the art. FIG. 5 (taken from Davies, D. Nature Reviews Drug Discovery, 2003, 2, 114-122) shows a generalized transgression of biofilm formation on a solid surface.

Assays on ESKAPE pathogens included MBEC assays and time kill assays. Determination of the mechanism of action included SEM imaging and molecular modeling.

TABLE 1 provides minimum biofilm eradication concentrations for mature biofilms (72 hr) of various ESKAPE Pathogens upon a 2-hour CAGE challenge.

TABLE 1

| Strain Species | Description | Notes | Concentration, % MBEC CAGE (v:v in $H_2O$) | MBEC CAGE (mM) |
|---|---|---|---|---|
| Staphylococcus aureus (MSSA) | Clinical isolate from sputum | Methicillin sensitive | 0.625 | 14.2 |
| Staphylococcus aureus (MRSA-6400) | Clinical isolate from sputum | Methicillin resistant | 0.317 | 7.11 |
| Staphylococcus aureus (MRSA-6404) | Clinical isolate from sputum | Methicillin resistant | 0.625 | 14.2 |
| Staphylococcus aureus (MRSA-6450) | Clinical isolate from blood | Methicillin resistant | 0.317 | 7.11 |
| Staphylococcus aureus (MRSA-6464) | Clinical isolate from nasal swab | Methicillin resistant | 0.317 | 7.11 |
| Staphylococcus aureus (MRSA-6522) | Clinical isolate from nasal swab | Methicillin resistant | 0.625 | 14.2 |
| Pseudomonas aeruginosa | Clinical isolate from sputum | | 10.0 | 227 |
| Enterobacter cloacae | Clinical isolate from blood | | 0.317 | 7.11 |
| Enterococcus sp. | Clinical isolate from wound | | 0.625 | 14.2 |
| Escherichia coli BL21 (DE3) | Commercially available (Life Technologies) | | 1.25 | 28.4 |
| Escherichia coli BL21-pet28A pET28A-eilA/R$^1$R | Expresses EilA/R efflux system | Resistant to imidazolium ILs | 2.5 | 56.9 |
| Escherichia coli BL21-pet28A pET28A-fsr | Expresses Fsr efflux system | Exhibits tolerance to phosphonium ILs | 1.0 | 22.7 |
| Acinetobacter baumanii | | | 0.625 | |
| Klebsiella pneumoniae | | | 1.25 | |

*E. coli* BL21-pet28A pET28A-eilA/R$^1$R is a strain that is known to be resistant to imidazolium ionic liquids. See Ruegg. Thomas L., Eun-Mi Kim, Blake A. Simmons, Jay D. Keasling, Steven W. Singer, Taek Soon Lee, and Michael P. Thelen, "An Auto-inducible Mechanism for Ionic Liquid Resistance in Microbial Biofuel Production." Nature Communications Nat Comms 5 (2014). *E. coli* BL21-pet28A pET28A-fsr is a strain that exhibits resistance to phosphonium ionic liquids.

Figure 6:
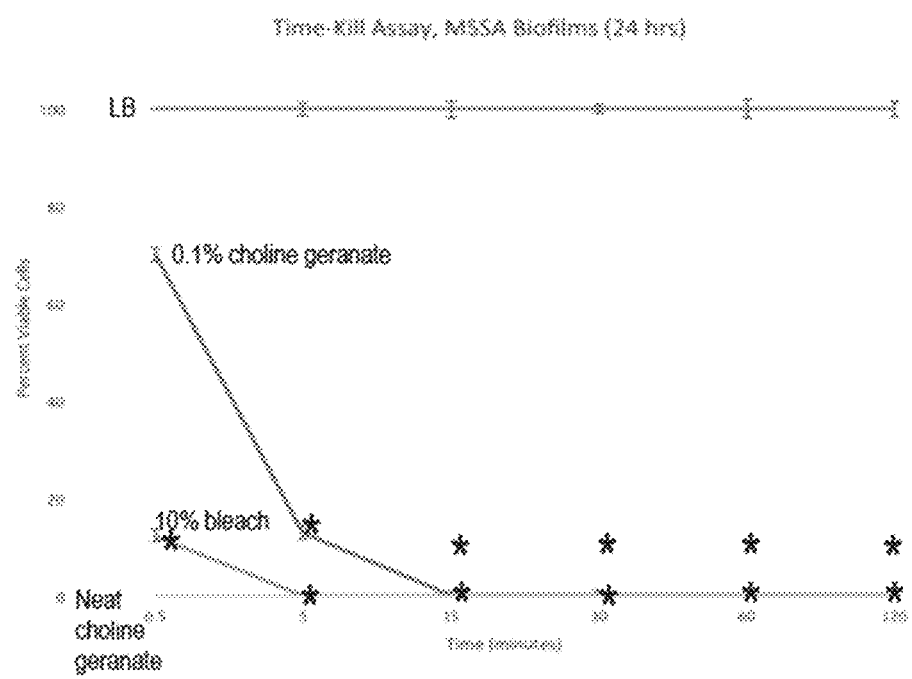
FIG. 6 provides time-kill assay plots for MSSA biofilms (24 hrs).

Time-Kill Assay Plots for MSSA Biofilms are provided in FIG. 6. Challenges were performed at 0.5 min, 5 min, 15 min, 30 min, 60 min, and 120 min. Reduction of biofilm viability of >99% with 0.1% CAGE in water occurred in 15 minutes for the 24 Hr biofilm, with 99.9% reduction achieved in 30 minutes. Statistical significance ($p<0.05$) is indicated with an asterisk.

Figure 7:
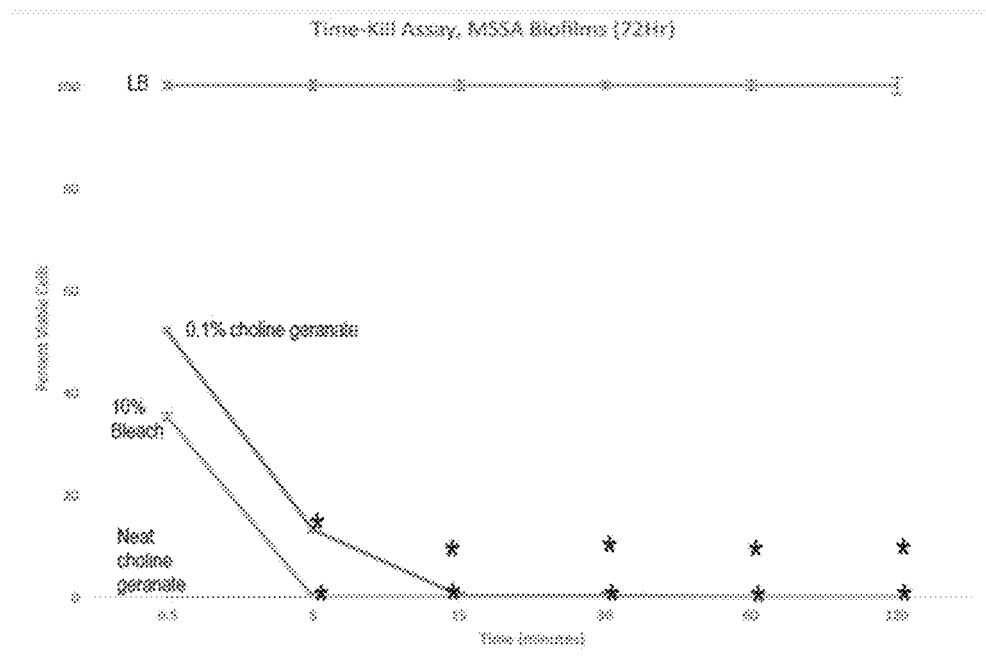
FIG. 7 provides time-kill assay plots for MSSA biofilms (72 hrs).

Reduction of biofilm viability of >99% with 0.1% CAGE in water occurred in 30 minutes for the 72 Hr biofilm, as shown in FIG. 7. Statistical significance ($p<0.05$) is indicated with an asterisk.

Figure 8:
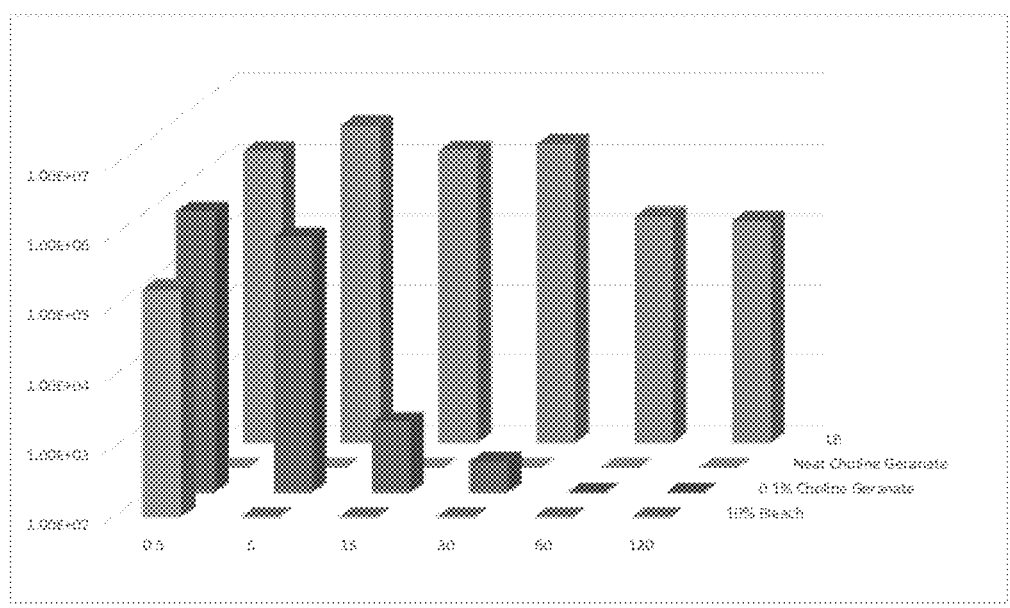
FIG. 8 depicts a representative plot of total viable cells within 24 hr MSSA biofilms versus exposure time for various CAGE concentrations.

The Minimal Biofilm Eradication Concentration (MBEC) or "Calgary method" was employed for biofilm growth and assessment of antibiofilm efficacy. Bacterial strains were grown for either 24 or 72 hours in Biofilm inoculators (MBEC plates; Innovotech, Calgary, CA) using published procedures. General Method: 200 μL of each IL/DES in tested panels was transferred to each well of the 96-well plate and the PEG lid harboring the respective biofilm carefully replaced and sealed with a gas permeable membrane. Following a two hour incubation at 37° C. with shaking at 120 rpm, the biofilm released from the PEG lid into a fresh 96-well plate by sonication with a Misonix® 3000 ultrasonic disruptor fitted with a microplate horn. Cell viability was assessed by enumeration on LB agar plates for the time-kill assay and by reading the optical density after a 24 hr incubation (37° C.; 180 rpm) for the MBEC assay. As a general trend, early stage biofilms (grown for 24 hours) were more susceptible to neutralization than the mature (72 hr) biofilms when exposed to neat IL/DESs over the two-hour period. FIG. 8 depicts a representative plot of total viable cells within 24 hr MSSA biofilms versus exposure time for various CAGE concentrations. The lower limit of detection for this assay is approximately 1000 cfu/mL. A 99.9% reduction occurred in ~5 min for bleach and 30 minutes for CAGE.

Figure 9A:
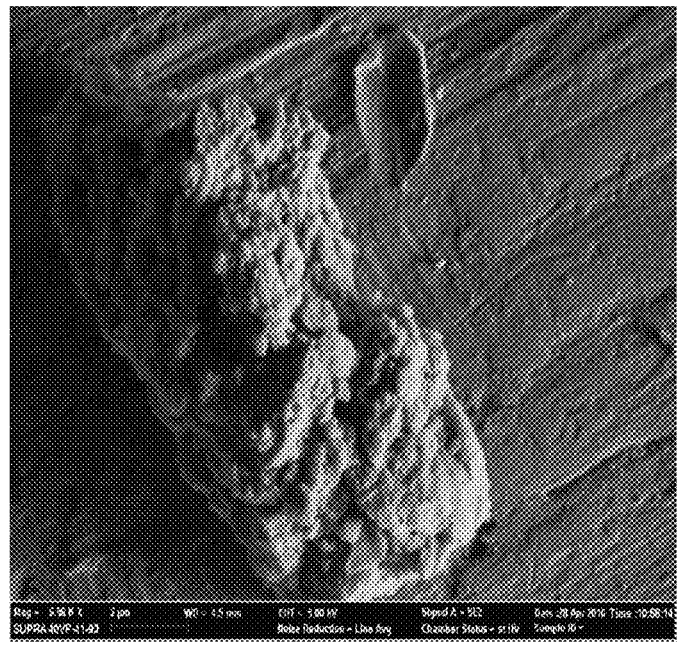
FIGS. 9A-9C provide SEM images of 72 hr MSSA biofilms on titanium coupons treated with 0.1% CAGE (control, FIG. 9A), (5 min, FIG. 9B), and (120 min, FIG. 9C).
Figure 9B:
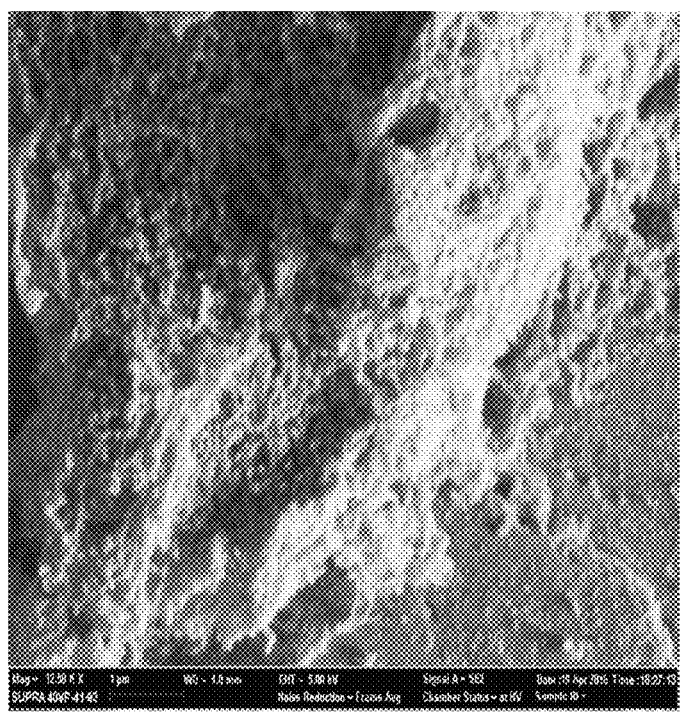
Figure 9C:
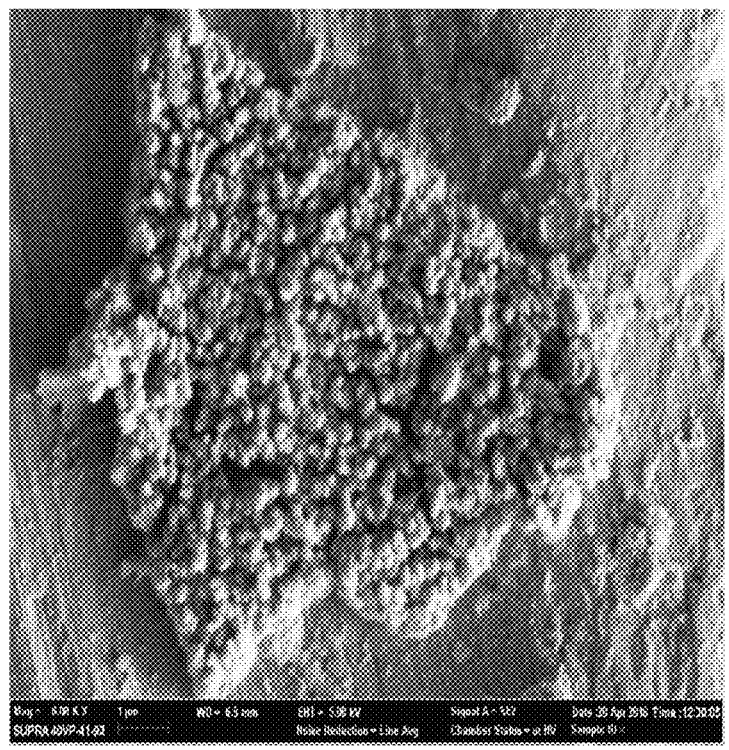

SEM images of 72 hr MSSA biofilms on titanium coupons treated with 0.1% CAGE for various times. All images were taken with 5 kV, Wd 4.5 mm. Magnification: 2200× (control, FIG. 9A), 1850× (5 min, FIG. 9B), and 8080× (120 min, FIG. 9C). Disruptions, or "tears", in the exopolymeric biofilm matrix become visible after 5 minutes of exposure to 0.1% CAGE. These "tears" appear as holes through which coccus bacteria previously located within the biofilm can be visualized.

Most ESKAPE pathogens show MBEC values between 0.3 and 1.25% CAGE; however, some are more resilient. For example, *P. aeruginosa* requires 10% CAGE for full eradication. Time-kill assays demonstrated a 99% reduction in biofilm viability within 30 minutes with 0.1% CAGE challenged against a mature biofilm. SEM images show tears/destruction of biofilm within 5 minutes, as measured by the ability to visualize coccoid bacteria from the matrix at these exposure times. Molecular modeling of other ionic liquids (imidazolium, in particular) indicate that overloading the outer leaflet results in membrane cavitation and cell disruption. This mechanism generally parallels that of other cationic antiseptics. Contrary to these observations, modeling of CAGE shows that both leaflets are populated by the DES, and that cells are neutralized without being disrupted. This prediction is consistent with observations that CAGE neutralized bacterial cells are killed without lysing (disruption).

Broad-Spectrum Antiseptic Activity

Choline and geranate deep eutectic solvent (or CAGE) is a novel material that has been demonstrated to display broad-spectrum antiseptic activity. CAGE is capable of penetration into the dermis after a topical application and the compound has also been shown to be effective against biofilms both in vitro and within the skin. The development of new treatments for skin infections are a high priority, given the large annual economic burden associated with treatment of these maladies and due to the emergence of pathogens resistant to current antibiotics. The goal of this work was to assess the efficacy of CAGE on pathogens associated with skin disease, including multidrug-resistant organisms.

Biofilms (72 hrs old) of *Staphylococcus aureus, Pseudomonas aeruginosa, Enterobacter cloacae, Enterococcus* sp, *Escherichia coli* and methicillin-resistant *Staphylococcus aureus* were cultured in cation-adjusted Mueller-Hinton broth (CAMHB) upon the pegs of a 96-well MBEC™ (Innovotech) assay plate. The antibiofilm activity of CAGE was evaluated as the minimal solution concentration required eradicating mature biofilms after a short (2 hr) exposure. Quantitation of viable cells within a biofilm as a function of exposure time was performed by first disruption of the biofilms with sonication followed dilution and enumeration on a solid medium (LB agar or MH agar). All biological experiments were performed a minimum of six times.

CAGE exhibited significant antibiofilm activity against most examined strains, including five clinical MRSA isolates. Mature biofilms of methicillin-sensitive *S. aureus* (MSSA) and *E. coli* were eradicated at solution concentrations of 0.625% and 1.25% (v:v), respectively. Time-kill assays showed that even short exposures (30 minutes) of dilute CAGE (0.1% v:v) to in vitro biofilms resulted in a reduction of viable cells within the biofilms of most strains by 1-2 $\log_{10}$ CFU in minutes.

Results show that dilute formulations of CAGE are effective at eliminating mature biofilms of various pathogens in vitro. While some ionic liquids/deep eutectic solvents are known to be disruptive to recalcitrant biopolymers (such as the protective exopolymeric layer which encapsulates most biofilms), molecular modeling experiments have provided new insights into the observed antibacterial effect of CAGE.

The geranic acid/geranate ion within CAGE is lipophilic, and like other hydrocarbons, can associate with a membrane readily. This is accepted knowledge for some isoprenoid compounds. It is believed that the lipophilicity of CAGE is at the root of its biological activity. This has been discussed as a factor for other antibiotic IL although it has not been stated this way for CAGE per se. Like other isoprenoids (e.g., cholesterol), the hydrophobic nature of geranate/geranic acid allows for insertion into a membrane and ultimately a high enough concentration of these compounds may modulate the membranes ability to function normally. This modulation of membrane composition is expected to indiscriminately affect natural processes that occur within the membrane (such as the action of requisite membrane enzymes).

Mechanism of Antibacterial Action of Imidazolium Ionic Liquids (1:1 Anion to Cation Ratio)

Figure 10:
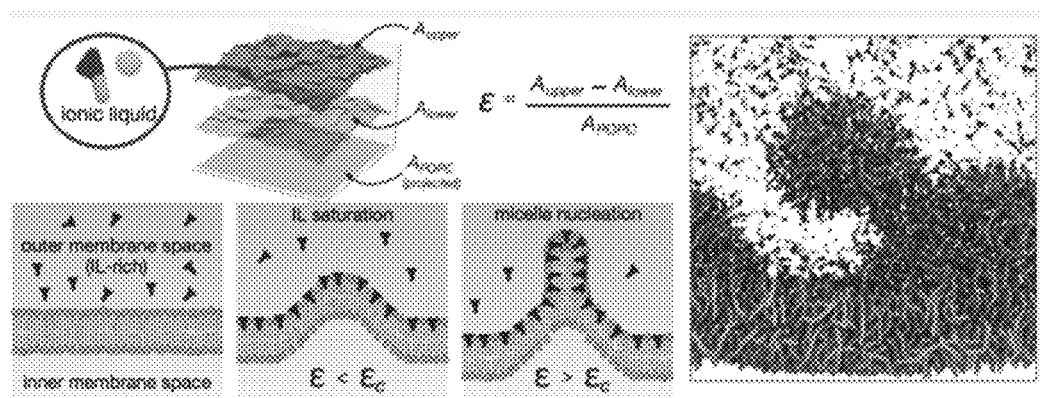
FIG. 10 depicts a process wherein cell disruption can be effected by an overload of IL into the outer leaflet, which causes membrane deformation, strain and eventually breakage.

The lipophilic ions of other ionic liquids are reported to populate the leaflet of the membranes that they encounter. The polar head group of the cation aligns with the phospholipid head groups of the leaflet, and the alkyl tail of the imidazolium cation with the fatty acid components of the membrane. A recent report suggests cell disruption can be effected by an overload of IL into the outer leaflet, which causes membrane deformation, strain and eventually breakage. See, e.g., FIG. 10 from Yoo et al, *Langmuir*, 2016, 32, 5403-5411

Mechanism of Antibacterial Action of a CAGE Deep Eutectic Solvent (1:1:1 Anion to Cation to Neutral Species Ratio)

Figure 11A:
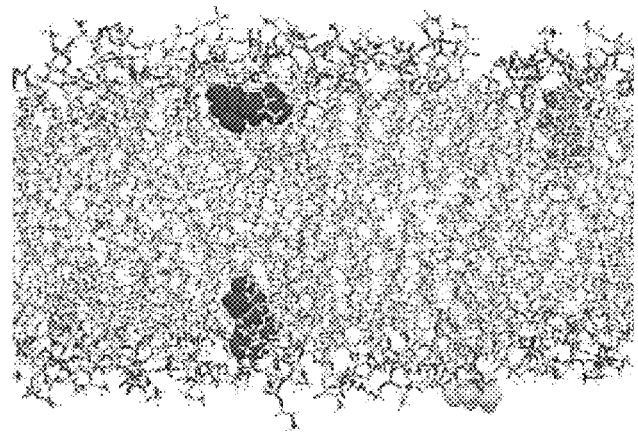
FIG. 11A depicts 1% CAGE in equilibrium with a palmitoyloleoyl phosphatidyl ethanolamine (POPE) model membrane.
Figure 11B:
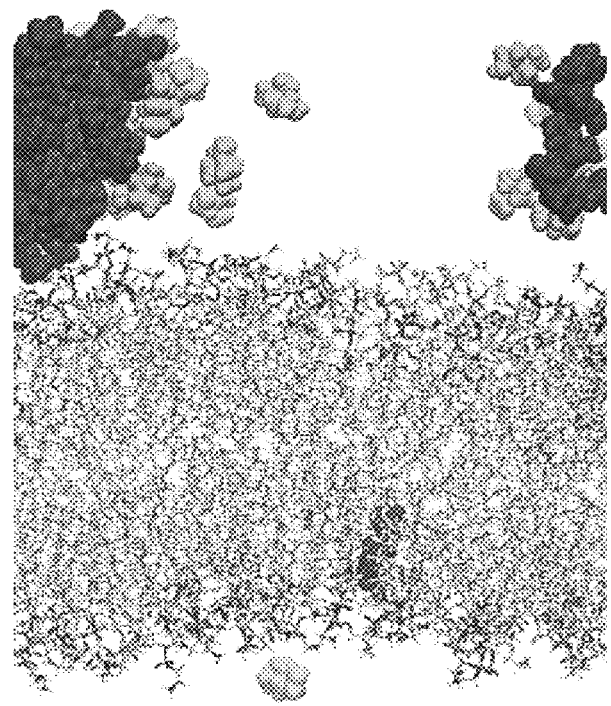
FIG. 11B depicts 10% CAGE in equilibrium with a palmitoyloleoyl phosphatidyl ethanolamine (POPE) model membrane.

The lipophilicity of CAGE is believed to be at the root of its biological activity. Modeling studies (Lindberg/Baker labs) indicate CAGE inserts into membrane and populates both leaflets of bilayer. The geranate anion aligns with the leaflet it encounters with the deprotonated acid near the phospholipid head groups and isoprenoid tail within the membrane. Geranic acid has no molecular charge and is able to diffuse from one leaflet to the other. In the figure below, the geranic acid (red) is observed in both leaflets at concentrations already known to be biologically effective. FIG. 11A depicts 1% CAGE in equilibrium with a palmitoyloleoyl phosphatidyl ethanolamine (POPE) model membrane, while FIG. 11B depicts 10% CAGE in equilibrium with a palmitoyloleoyl phosphatidyl ethanolamine (POPE) model membrane.

It is believed that CAGE DES populates both leaflets of the membrane bilayer (the layer the material physically encounters in a biological assay, and then diffuses to the inner leaflet it does not directly encounter). It is believed that the acid component in CAGE DES enables more thorough saturation of both leaflets of the membrane than an IL itself (although CAGE IL also has antibiofilm activity). This mechanism is supported by the observation that, unlike imidazolium IL, CAGE DES treatment of bacterial cells does not elicit cell disruption. (See Zakrewsky et al., Advanced Healthcare Materials, 2016, 5, 1282-1289; CAGE treated cells are inactivated but the cells themselves remain intact).

Higher concentrations of inserted CAGE also correlate to a computationally predicted thinning of the membrane, which may also result in deleterious effects on membrane proteins. Neutral species in DES may be uniquely important to potentiate otherwise bioactive IL. Potentially the isoprenoid acids examined may also have unique antibiofilm activity in this regard, and may potentiate otherwise inactive IL when formed as a DES. Other DES including isoprenoid acids other than geranic acid are demonstrated to have similar antibiofilm activities as CAGE and can be used as components of new antibiotic formulations. DES of choline citronellate has been tested and its MBEC against MSSA is 0.625% in water. This is approximately the same value that CAGE has against this strain. It has been shown that geranic acid in solution (50 mM Hepes buffer, pH=6.4, 0.1% Tween 20) has a fairly low MBEC value (2.5% in water). At this pH, most of the acid is expected to be found in the protonated state (pKa is ~5-5.5 according to the literature). However, when the pH is raised by two units to 8.4 (50 mM Hepes buffer, pH=8.4, 0.1% Tween 20), the value for the MBEC is >10%. The ratio of geranate anion to geranic acid is 100× greater at pH 8.4 relative to 6.4, which is consistent with the neutral species (in this case, protonated geranic acid) component plays an important antibacterial role within the DES. This experimental data validates the hypothesis generated after analysis of the molecular models of CAGE/membrane interactions. The geranate anion is also antibacterial. CAGE IL (1:1 geranate anion to cholinium cation) has an MBEC of 5-10% in water against MSSA whereas the CAGE DES (1:1:1 geranate anion to cholinium cation to geranic acid neutral species) displays an MBEC of 0.625%. Many different DES can be envisioned with this same platform of 1:1 anion:cation as an EPS disruptor/delivery agent with a neutral acid (or even a completely neutral species such as an isoprenoid hydrocarbon) as a molecule designed to saturate both leaflets of a cellular membrane. Accordingly, IL can be good antibiofilm agents, but formulation as a DES (with the neutral species being various species) can make them even more effective antibiofilm agents.

Molecular-Scale Effects of CAGE on POPE Membranes

Figure 12A:
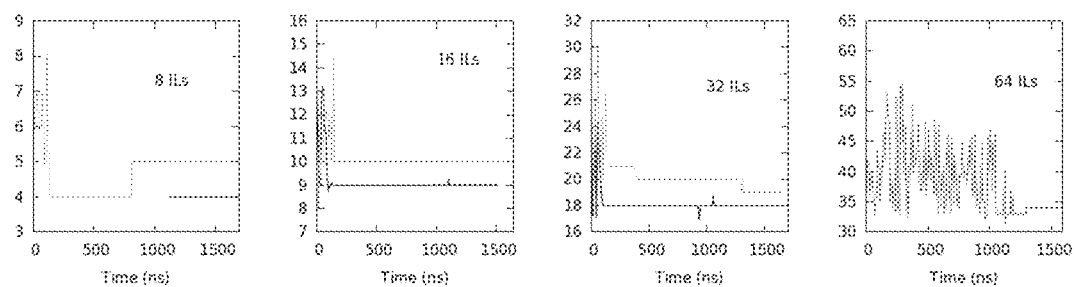
FIG. 12A is a graph depicting the number of geranate ions in one of the membrane bilayer leaflets for two replicate simulations each.
Figure 12B:
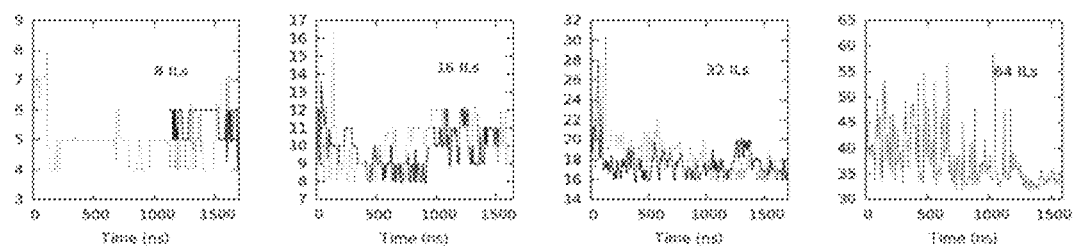
FIG. 12B is a graph depicting the number of geranic acid molecules in one of the membrane bilayer leaflets for two replicate simulations each.

The following graphs depict the number of geranate ions (FIG. 12A) or geranic acid molecules (FIG. 12B) in one of the membrane bilayer leaflets for two replicate simulations each. The number of geranate ions is found to fluctuate between the leaflets until the membrane stabilizes and then transfer between leaflets is rare. The geranic acid, however, is seen to readily flip between leaflets even after the membrane stabilizes.

Figure 13:
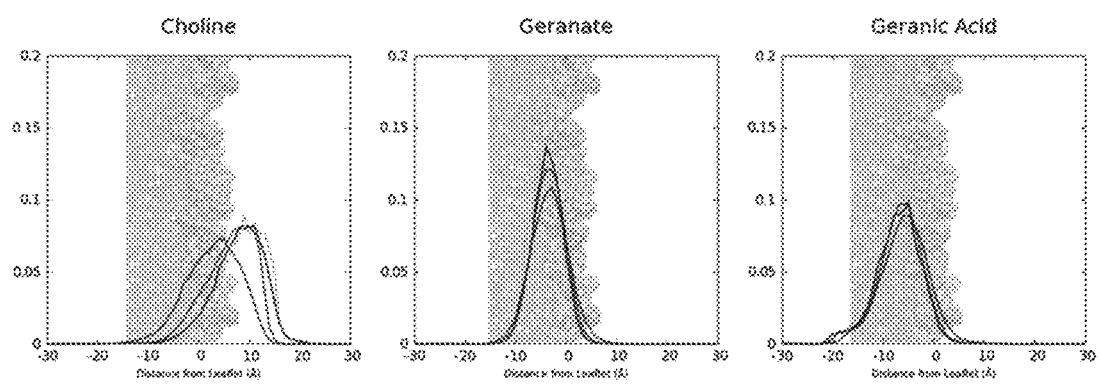
FIG. 13 depicts a leaflet illustrating densities, where the atoms in the head groups are depicted with gold spheres and the atoms in the hydrophobic tails are shown as grey spheres.

The position of the IL components relative to the bilayer is shown in the following three plots. The 8 CAGE system is cyan, the 16 CAGE system is blue, the 32 CAGE systems is brown, and the 64 CAGE system is red. A representative snapshot of one leaflet is shown in FIG. 13 to help illustrate the densities, where the atoms in the head groups are depicted with gold spheres and the atoms in the hydrophobic tails are shown as grey spheres. Choline is found to populate the aqueous phase while geranate and geranic acid embed within the hydrophobic core of the bilayer. The deprotonated oxygen of geranate remains near the lipid-water interface, while geranic acid has greater density deeper in the hydrophobic tail region.

TABLE 2 provides information regarding the effect of IL concentration on bilayer physical properties. Further information is provided in Rappolt M., Hickel A., Bringezu F., Lohner K. Mechanism of the lamellar/inverse hexagonal phase transition examined by high resolution X-ray diffraction. Biophys. J. 2003, 8453111-3122; and Rand R. P., Parsegian V. A. Hydration forces between phospholipid bilayers. Biochim. Biophys. Acta 1989, 9883351-376, the contents of which are hereby incorporated by reference in their entireties.

TABLE 2

| POPE | Volume per Lipid, Å$^3$ | Bilayer Thickness, Å | $K_a$ mN/m | Area per Molecule, Å$^2$ | Roughness |
|---|---|---|---|---|---|
| Exp. | 1175[1] | 39.5[1] | 233[2] | 5960,[1] 56.6[2] | N/A |
| 0 | 1158(6.13) | 42.38 ∓ 0.863 | 528 | 55.57 ∓ 1.38 | 1.55 ∓ .25 |
| 8 | 1098 ∓ 5.75 | 41.58 ∓ 1.08 | 409 | 52.47 ∓ 1.36 | 1.70 ∓ .39 |
| 16 | 1038 ∓ 6.10 | 40.35 ∓ 0.814 | 984 | 50.30 ∓ 1.10 | 1.75 ∓ 0.44 |
| 32 | 918 ∓ 6.20 | 38.66 ∓ 0.794 | 1056 | 47.01 ∓ 1.03 | 1.83 ∓ 0.38 |
| 64 | 675 ∓ 6.44 | 36.28 ∓ 1.17 | 3131 | 42.44 ∓ 0.796 | 1.93 ∓ 0.44 |

Simulation Details

The structures of choline, geranate, and geranic acid were created using LeAP, from the AmberTools suite of programs. The structures of POPE were obtained from the CHARMM-GUI. Packmol was used to generate random initial configurations of 128 lipids, 3968 waters, and the desired concentration of IL. Lipid interactions were modeled with the AMBER lipid14 force field and water with the TIP3P model. CAGE was modeled with the general AMBER force field, with charges scaled by 0.8.

Molecular dynamics simulations of the self-assembly of POPE phospholipid bilayers with different concentrations of the ionic liquid choline-geranate were performed with AMBER version 14. The Langevin thermostat with a collision frequency of 1.0 ps$^{-1}$ was used with a reference temperature of 303 K and the berendsen barostat was employed to maintain pressure at 1 bar. SHAKE was used to restrain bonds involving hydrogen. Short range VDW interactions were evaluated up to a cutoff of 8.0 angstroms and the particle mesh Ewald method was used to evaluate long range electrostatic interactions. Minimization and initial equilibration steps were done using the CPU implementation of sander and subsequent steps were performed using the GPU implementation of pmemd. First, each system was minimized for 10,000 step. Second, each system was equilibrated with a timestep of 0.5 fs for 5 ns. This step was performed with the parallel CPU implementation of pmemd. The time step was then increased to 1 fs for 2 ns, and then 2 fs for the remaining 1 μs isotropic NPT simulation. Previously a similar study used shorter duration isotropic equilibration simulations. Early attempts to introduce anisotropic NPT resulted in the simulation cell becoming elongated and the simulation failing. This was alleviated by extending the duration of the isotropic NPT equilibration simulation, before initiating the anisotropic production. Last, each system was propagated for at least 500 ns with the anisotropic barostat. The 32-PC and 64-PC systems were simulated for a total of 2 μs anisotropic NPT because of the slower or nonexistent bilayer assembly time in those systems.

The number of ILs in each leaflet was calculated by comparing the distance of the same terminal oxygen atoms to the average position of each leaflet, the IL was considered to be a part of the leaflet which it was nearest to.

Volume per lipid was calculated according to the following equation:

$$V_L = \frac{V_{box} - N_{wat}V_{wat} - N_{IL}V_{IL}}{N_L} \quad (1)$$

Where N is the number, V is the volume, and the subscripts box, wat, IL, and L refer to the system box, water, ionic liquid, and lipid, respectively. The value for the volume of water was obtained from Madej et al. The volume of each IL molecule was calculated using the VABC method. The bilayer thickness was calculated every 200 ps, by evaluating the difference between the average position of the phosphorous atoms in the lipid head groups in each leaflet. The area per molecule was calculated by doubling the lateral area to account for both leaflets and dividing by the total number of lipids plus the number of ILs embedded in the bilayer.

The isothermal compressibility moduli, $K_a$, is a measure of the resistance of the bilayer to deformation. Ka is calculated according to $$K_A = \frac{2k_B T \langle A_L \rangle}{N_L \sigma_A^2} \quad (2)$$

Where $k_B$ is Boltzmann's constant, T is temperature $\langle A_L \rangle$ is the average area per lipid, NL is the number of lipids, and $\sigma_A^2$ is the variance of the area per lipid. The last 100 ns of each simulation were used to calculate all of these values. The membrane roughness was calculated according to equation 3.

$$R = \frac{1}{N_L} \Sigma(z - z_\mu) - \quad (3)$$

Where $n_l$ is the number of lipids, z is the coordinate of the phosphorous atom of each lipid in the dimension of the bilayer normal and $z_\mu$ is the average position of the phosphorous atoms in each leaflet.

The preferred positions of the ionic liquid were calculated by finding the distance between the terminal oxygen atoms in geranate and geranic acid, and the nitrogen in choline and the average position of the phosphorous atoms in nearest leaflet in the Z dimension. A positive value represents the outside of the bilayer, while a negative value represents the inside of the bilayer. The values reported are averages over each anisotropic simulation.

General Synthetic Methods for Synthesis of Novel Deep Eutectic Solvents, Eutectic Mixtures and Binary Mixtures Representative DES reported here were synthesized via salt metathesis in a manner similar to that reported for the synthesis of choline geranate (CAGE, 1). Recrystallization of geranic acid and synthetic reactions using this material were conducted away from light by covering reaction vessels with foil. Conductance was recorded using a CT-3013 conductivity meter and proton and carbon nuclear magnetic resonance ($^1$H NMR) recorded using a 500 MHz Oxford NMR. Chemical shifts are reported on a scale of 0-14 δ (ppm) and coupling constants (J) are reported in Hz. Splitting patterns are described as s, singlet; d, doublet; t, triplet; m, multiplet; and br, broad singlet. The carbon nuclear magnetic resonance signals were recorded on a scale of 0-200 ppm.

In general, syntheses of novel DES, eutectic mixtures and binary mixtures were formed by first synthesizing an ionic liquid (1:1 molar equivalents of cation and anion moieties) from choline bicarbonate and an alkyl acid (such as geranic or citronellic acid), which was then concentrated in vacuo and dried on a vacuum oven. Aliquots of the resultant ionic liquid were then mixed with volumes of the appropriate neutral species (equimolar amounts of neutral species as cationic or anionic moieties in the ionic liquid) with mild heating to afford the DES, eutectic mixtures and binary mixtures. Alternatively, these materials may also be formed by addition of the neutral species to choline bicarbonate and alkyl acid during the salt metathesis reaction, followed by concentration and vacuum drying.

Synthesis of Choline Geranate Ionic Liquid (1:1 CAGE, 2)

Choline bicarbonate (80 wt % solution, 10.02 g, 0.061 mol) was added dropwise to recrystallized geranic acid (10.2 g, 0.061 mol) and the mixture was stirred at room temperature, covered, until evolution of $CO_2$ had ceased (typically 24 hours). At this time, the reaction mixture was concentrated in vacuo using a rotary evaporator and dried on a vacuum oven (60° C.) for 12-24 hours. A total of 6.50 g of 2 as a viscous yellow syrup was recovered after removal from the vacuum. The conductance was observed to be 40 μS. $^1$H NMR (CDCl$_3$): δ 5.61 (s, 1H), 5.03 (t, J=6.4, 1H), 3.99 (bs, 2H), 3.61 (t, J=4.8, 2H), 3.27 (s, 9H), 2.02 (m, 2H), 1.93 (s, 5H), 1.65 (s, 1H), 1.59 (s, 3H), 1.52 (s, 3H).

Synthesis of Choline Citronellate Ionic Liquid (1:1 CACI, 3)

Choline bicarbonate (80 wt % solution, 11.64 g, 0.070 mol) was added dropwise to citronellic acid (12.0 g, 0.070 mol) and the mixture was stirred at room temperature, covered, until evolution of $CO_2$ had ceased (typically 24 hours). At this time, the reaction mixture was concentrated in vacuo using a rotary evaporator and dried on a vacuum oven (60° C.) for 12-24 hours. A total of 6.50 g of 3 as a very viscous yellow syrup was recovered after removal from the vacuum. The conductance was observed to be 40 μS. $^1$H NMR (CDCl$_3$): δ $^1$H NMR (CDCl$_3$): δ 5.66 (s, 1H), 5.06 (t, J=6.4, 1H), 4.05 (bs, 2H), 3.65 (t, J=4.8, 2H), 3.3 (s, 9H), 2.18 (m, 2H), 1.99 (s, 3H), 1.96 (m, 1H), 1.62 (s, 3H), 1.55 (s, 3H).

Synthesis of Choline Geranate Citronellic Acid DES (4)

Choline bicarbonate (45 wt % solution, 10.1 g, 0.0275 mol) was added dropwise to recrystallized geranic acid (4.63, 0.0275 mol) and citronellic acid (4.69 g, 0.0275 mol) and the mixture was stirred at room temperature, covered, until evolution of $CO_2$ had ceased (typically 24 hours). At this time, the reaction mixture was concentrated in vacuo using a rotary evaporator and dried on a vacuum oven (60° C.) for 12-24 hours. A total of 11.84 g of 4 was isolated as a yellow oil. $^1$H NMR (CDCl$_3$): δ 5.61 (s, 1H), 5.06 (t, J=7.4, 1H), 4.06 (bs, 2H), 3.61 (t, J=4.8, 2H), 3.29 (s, 9H), 2.04 (m, 2H), 1.93 (s, 5H), 1.65 (s, 5H), 1.59 (s, 3H), 1.52 (s, 3H), 0.9 (d, J=6.5, 3H).

Synthesis of Choline Geranate Farnesol DES (5)

Farnesol (0.71 g, 0.00397 mol) was added in equimolar amounts to vacuum dried 2 (1.06 g, 0.00397 mol) in a 20 mL vial with a stir bar. The reagents were subjected to mild heating (30° C.) and were stirred until heterogeneity of the mixture was observed with a concomitant increase in fluidity. A total of 1.77 g of 5 was isolated as a yellow oil. $^1$H NMR (CDCl$_3$): δ 5.67 (s, 1H), 5.07 (t, J=6.4, 1H), 4.11 (d, J=6.8, 2H) 4.00 (bs, 2H), 3.66 (t, J=4.8, 2H), 3.27 (s, 11H), 2.06 (m, 4H), 2.00 (s, 5H), 1.65 (s, 1H), 1.64 (s, 5H), 1.6 (s, 4H).

Synthesis of Choline Geranate Linalool DES (6)

Linalool (0.64 g, 0.00412 mol) was added in equimolar amounts to vacuum dried 2 (1.37 g, 0.00412 mol) in a 20 mL vial with a stir bar. The reagents were subjected to mild heating (30° C.) and were stirred until heterogeneity of the mixture was observed with a concomitant increase in fluidity. A total of 2.01 g of 6 was isolated as a yellow oil. $^1$H NMR (CDCl$_3$): δ 5.9 (dd, J$^1$=17.3, J$^2$=10.7, 1H), 5.66 (s, 1H), 5.15 (d, J=17.3, 1H), 5.07 (t, J=6.4, 1H), 5.02 (d, J=10.7, 1H), 4.06 (bs, 5H), 3.66 (t, J=4.8, 5H), 3.27 (s, 21H), 2.06 (m, 5H), 1.99 (s, 10H), 1.65 (s, 10H), 1.56 (s, 10H), 1.23 (s, 5H).

Synthesis of Choline Geranate Geraniol DES (7)

Geraniol (0.54 g, 0.00349 mol) was added in equimolar amounts to vacuum dried 2 (1.16 g, 0.00349 mol) in a 20 mL vial with a stir bar. The reagents were subjected to mild heating (30° C.) and were stirred until heterogeneity of the mixture was observed with a concomitant increase in fluidity. A total of 1.7 g of 7 was isolated as a yellow oil. $^1$H NMR (CDCl$_3$): δ 5.66 (s, 1H), 5.35 (t, J=6.4, 1H), 5.06 (m, 2H), 4.1 (d, J=6.8, 2H) 4.06 (bs, 2H), 3.65 (t, J=4.8, 2H), 3.27 (s, 10H), 2.06 (m, 3H), 1.99 (s, 5H), 1.62 (s, 1H), 1.59 (s, 6H), 1.52 (s, 3H).

Synthesis of Choline Geranate Eugenol DES (8)

Eugenol (0.48 g, 0.00292 mol) was added in equimolar amounts to vacuum dried 2 (0.97 g, 0.00292 mol) in a 20 mL vial with a stir bar. The reagents were subjected to mild heating (30° C.) and were stirred until heterogeneity of the mixture was observed with a concomitant increase in fluidity. A total of 1.45 g of 8 was isolated as a light brown oil. $^1$H NMR (CDCl$_3$): δ 6.89 (d, J=7.9, 1H), 6.62 (s, 1H), 6.60 (d, J=8, 1H), 5.91 (m, 1H), 5.7 (s, 1H), 5.61 (s, 1H), 5.05 (t, J=6.4, 2H), 5.01 (s, J=7.7, 1H) 4.03 (bs, 3H), 3.79 (s, 3H), 3.61 (t, J=4.8, 3H), 3.27 (s, 18H), 2.06 (m, 3H), 2.01 (s, 5H), 1.71 (s, 1H), 1.63 (s, 4H), 1.56 (s, 3H).

Synthesis of Choline Geranate Cinnamaldeyde DES (9)

Cinnamaldehyde (0.45 g, 0.00337 mol) was added in equimolar amounts to vacuum dried 2 (1.12 g, 0.00337 mol) in a 20 mL vial with a stir bar. The reagents were subjected to mild heating (30° C.) and were stirred until heterogeneity of the mixture was observed with a concomitant increase in fluidity. A total of 1.57 g of 9 was isolated as a dark brown oil. $^1$H NMR (CDCl$_3$): δ 9.66 (d, J=7.7, 1H), 8.67 (s, 1H), 8.62 (bs, 5H), 7.54 (dd, J=6.6, 2H), 7.5 (d, J=16, 2H), 7.39 (m, J=3), 6.7 (dd, J=7.7, 1H), 5.66 (s, 4), 5.03 (t, J=6.4, 3H), 4.00 (bs, 8H), 3.59 (t, J=4.8, 8H), 3.27 (s, 37H), 2.02 (m, 8H), 1.93 (s, 16H), 1.72 (s, 2H), 1.61 (s, 10H), 1.54 (s, 10H), 1.52 (s, 3H).

Synthesis of Choline Geranate Cinnamic Acid DES (10)

Cinnamic acid (0.74 g, 0.0050 mol) was added in equimolar amounts to vacuum dried 2 (1.67 g, 0.0050 mol) in a 20 mL vial with a stir bar. The reagents were subjected to mild heating (30° C.) and were stirred until heterogeneity of the mixture was observed with a concomitant increase in fluidity. A total of 2.41 g of 10 was isolated as a yellow oil. $^1$H NMR (CDCl$_3$): δ 9.79 (s, 2H), 7.45 (t, J=6.7, 2H), 7.29 (q, J=7.3, 2H), 6.56 (d, J=16, 1H), 5.71 (s, 1H), 5.05 (t, J=6.4, 1H), 4.07 (bs, 2H), 3.65 (t, J=4.8, 2H), 3.27 (s, 10H), 2.08 (m, 2H), 2.06 (s, 5H), 1.8 (s, 1H) 1.64 (s, 3H), 1.56 (s, 3H).

Synthesis of Choline Geranate β-Citronellol Acid DES (11)

β-citronellol (0.45 g, 0.00289 mol) was added in equimolar amounts to vacuum dried 2 (0.96 g, 0.00289 mol) in a 20 mL vial with a stir bar. The reagents were subjected to mild heating (30° C.) and were stirred until heterogeneity of the mixture was observed with a concomitant increase in fluidity. A total of 1.41 g of 11 was isolated as a yellow oil. $^1$H NMR (CDCl$_3$): δ 5.65 (s, 1H), 5.05 (t, J=6.4, 1H), 4.03 (bs, 2H), 3.63 (t, J=4.8, 2H), 3.57 (m, 1H), 3.27 (s, 8H), 2.04 (m, 2H), 1.98 (s, 4H), 1.62 (s, 4H), 1.54 (s, 4H), 1.3 (m, 2H), 1.1 (m, 1H), 0.84 (d, J=6.6, 2H).

Synthesis of Choline Geranate Terpineol (12)

Terpineol (0.65 g, 0.00421 mol) was added in equimolar amounts to vacuum dried 2 (1.40 g, 0.00421 mol) in a 20 mL vial with a stir bar. The reagents were subjected to mild heating (30° C.) and were stirred until heterogeneity of the mixture was observed with a concomitant increase in fluidity. A total of 2.05 g of 12 was isolated as a yellow oil. $^1$H NMR (CDCl$_3$): δ 5.67 (s, 1H), 5.06 (t, J=6.4, 1H), 4.04 (bs, 2H), 3.65 (t, J=4.8, 2H), 3.27 (s, 11H), 2.05 (m, 3H), 1.99 (s, 6H), 1.62 (s, 3H), 1.60 (s, 3H), 1.56 (s, 3H), 1.23 (m, 1H), 1.18 (s, 1H), 1.13 (d, J=6.1, 4H).

Synthesis of Choline Citronellate DES (13)

Citronellic acid (4.60 g, 0.027 mol) was added in equimolar amounts to vacuum dried 3 (6.50 g, 0.027 mol) in a 20 mL vial with a stir bar. The reagents were subjected to mild heating (30° C.) and were stirred until heterogeneity of the mixture was observed with a concomitant increase in fluidity. A total of 11.1 g of 13 was isolated as a yellow oil. $^1$H NMR (CDCl$_3$): δ 5.85 (s, 4H), 5.06 (t, J=7.1, 1H), 4.02 (bs, 2H), 3.59 (t, J=6.8, 2H), 3.25 (s, 8H), 2.21 (m, 1H), 1.94 (m, 5H), 1.64 (s, 3H), 1.56 (s, 3H), 1.31 (m, 1H), 1.15 (m, 1H), 0.9 (d, 3H).

Synthesis of Choline Citronellate Farnesol DES (14)

Farnesol (0.94 g, 0.00422 mol) was added in equimolar amounts to vacuum dried 3 (1.41 g, 0.00422 mol) in a 20 mL vial with a stir bar. The reagents were subjected to mild heating (30° C.) and were stirred until heterogeneity of the mixture was observed with a concomitant increase in fluidity. A total of 2.35 g of 14 was isolated as a yellow oil. $^1$H NMR (CDCl$_3$): δ 5.36 (t, J=6.8, 1H), 5.07 (q, J=5.8, 3H), 4.1 (d, J=6.8, 2H), 4.06 (bs, 3H), 3.61 (t, J=4.8, 3H), 3.27 (s, 13H), 2.14 (m, 1H), 2.0 (m, 17H), 1.65 (d, J=8.8, 11H), 1.56 (d, J=6.8, 8H), 0.89 (d, J=6.2, 4H).

Synthesis of Choline Citronellate Linalool DES (15)

Linalool (0.70 g, 0.00455 mol) was added in equimolar amounts to vacuum dried 3 (1.52 g, 0.00455 mol) in a 20 mL vial with a stir bar. The reagents were subjected to mild heating (30° C.) and were stirred until heterogeneity of the mixture was observed with a concomitant increase in fluidity. A total of 2.22 g of 15 was isolated as a yellow oil. 1H NMR (CDCl$_3$): δ 5.88 (dd, J=17.5, 1H), 5.19 (dd, J=7.3, 1H), 5.08 (q, J=6.4, 3H), 5.03 (dd, J=10.8, 1H), 4.05 (bs, 4H), 3.67 (t, J=4.8, 4H), 3.32 (s, 19H), 2.17 (q, J=8.8, 2H), 1.96 (m, 4H), 1.86 (s, 7H), 1.64 (d, 9H), 1.56 (d, 9H), 1.50 (m, 3H), 1.24 (s, 6H), 0.89 (d, J=6.2, 6H).

Synthesis of Choline Citronellate Geraniol DES (16)

Geraniol (0.55 g, 0.00359 mol) was added in equimolar amounts to vacuum dried 3 (1.2 g, 0.00359 mol) in a 20 mL vial with a stir bar. The reagents were subjected to mild heating (30° C.) and were stirred until heterogeneity of the mixture was observed with a concomitant increase in fluidity. A total of 1.75 g of 16 was isolated as a yellow oil. $^1$H NMR (CDCl$_3$): δ 5.36 (t, J=7.8, 1H), 5.05 (t, J=7.0, 2H), 4.09 (d, J=6.7, 2H), 4.03 (bs, 4H), 3.64 (t, J=4.8, 3H), 3.27 (s, 16H), 2.16 (q, J=8.3, 1H), 2.04 (m, 3H), 2.02 (m, 1H), 1.96 (m, 4H), 1.88 (m, 5H), 1.63 (d, J=7.3, 11H), 1.56 (d, J=7.4, 7H), 1.3 (m, 2H), 1.22 (m, 2H), 0.89 (d, J=6.2, 5H).

Synthesis of Choline Citronellate Cinnamaldeyde DES (17)

Cinnamaldehyde (0.49 g, 0.00374 mol) was added in equimolar amounts to vacuum dried 3 (1.23 g, 0.00374 mol) in a 20 mL vial with a stir bar. The reagents were subjected to mild heating (30° C.) and were stirred until heterogeneity of the mixture was observed with a concomitant increase in fluidity. A total of 1.72 g of 17 was isolated as a dark brown oil. $^1$H NMR (CDCl$_3$): δ 9.67 (d, J=7.7, 1H), 8.67 (s, 1H), 7.54 (m, 2H), 7.47 (d, J=16, 1H), 7.4 (m, 3H), 6.71 (dd, J=16, 1H), 5.07 (t, J=7.1, 3H), 4.02 (bs, 7H), 2.19 (q, J=8.4, 3H), 1.92 (m, 13H), 1.61 (s, 9H), 1.54 (s, 8H), 1.31 (m, 3H), 1.12 (m, 5H), 0.89 (d, J=6.3, 11H).

Synthesis of Choline Citronellate β-Citronellol Acid DES (18)

β-citronellol (0.62 g, 0.00398 mol) was added in equimolar amounts to vacuum dried 3 (1.33 g, 0.00389 mol) in a 20 mL vial with a stir bar. The reagents were subjected to mild heating (30° C.) and were stirred until heterogeneity of the mixture was observed with a concomitant increase in fluidity. A total of 1.95 g of 18 was isolated as a yellow oil. $^1$H NMR (CDCl$_3$): δ 5.03 (t, J=6.4, 1H), 4.03 (bs, 2H), 3.65 (t, J=4.8, 2H), 3.58 (m, 1H), 3.27 (s, 8H), 2.16 (q, J=8.3, 1H), 1.9 (m, 4H), 1.63 (d, J=7.8, 4H), 1.55 (d, J=6.7, 5H), 1.31 (m, 2H), 1.13 (m, 2H), 0.89 (d, J=6.2, 2H), 0.86 (d, J=6.6, 2H).

Synthesis of Choline Citronellate Terpineol (19)

Terpineol (0.64 g, 0.00413 mol) was added in equimolar amounts to vacuum dried 3 (1.38 g, 0.00413 mol) in a 20 mL vial with a stir bar. The reagents were subjected to mild heating (30° C.) and were stirred until heterogeneity of the mixture was observed with a concomitant increase in fluidity. A total of 2.02 g of 19 was isolated as a yellow oil. $^1$H NMR (CDCl$_3$): δ 5.35 (bs, 1H), 5.07 (t, J=6.4, 1H), 4.05 (bs, 4H), 3.67 (t, J=4.8, 4H), 3.27 (s, 20H), 2.12 (q, J=8.2, 3H), 1.94 (m, 15H), 1.62 (s, 10), 1.55 (s, 1.55), 1.46 (m, 2H), 1.32 (m, 2H), 1.23 (m, 1H), 1.19 (s, 1H), 1.15 (d, J=6.2, 13H), 0.90 (d, 6.2, 7H).

General Procedure for Biofilm Culture

Biofilms of Methicillin-sensitive *Staphylococcus aureus* (MSSA) were established on the pegs of a biofilm inoculator (Innovotech) according to the manufacturer's instructions. Briefly, a bacterial colony of MSSA was inoculated from an agar streak plate into cation-adjusted Mueller-Hinton broth (5 mL) and grown to confluence overnight in a shaker incubator (37° C., 200 rpm). The confluent culture was then diluted into fresh media (1:100, v:v), and grown to an optical density (OD) of 0.4 (approximately three hours). At this time, the cultures were again diluted into fresh media (1:50, v:v) and 200 μL of the resultant dilution were placed into each well of an Innovotech 96 well biofilm inoculator plate. The inoculator was added to the wells of the culture plate and it was placed in a shaker incubator overnight (37° C., 150 rpm). The spent media was decanted each morning and refreshed with equal volumes of new media, and the inoculator was again placed in a shaker incubator overnight (37° C., 150 rpm). This procedure was repeated twice more to ultimately yield MSSA biofilms that had developed for three days (72 hr).

Determination of Minimum Biofilm Eradication Concentration (MBEC) for DES

A 10% (v:v) stock solution of each DES in CAMHB was serially diluted into fresh CAMHB in the wells of a 96 well plate. In this plate (DES challenge plate) each well contained a final solution volume of 150 μL in each well, and final DES solution concentrations ranged from 0.313-10% (v:v). The DES challenge plate also contained wells reserved for positive (CAMHB only) and negative (10% bleach) controls. At this time, the biofilm inoculator was removed from the culture 96 well plate, rinsed twice by immersing the inoculator in fresh CAMHB in a 96 well plate, and the inoculator was then immersed in the DES challenge solutions. Biofilms on the inoculator were challenged with the dilute DES for 2 hours at which time it was removed and rinsed with 50% ethanol in water (1×) and fresh CAMHB (2×). The inoculator was placed into a new 96 well plate filled with fresh CAMHB in each well (150 μL), and wrapped with parafilm. Biofilms on the inoculator were disrupted via sonication (20 minutes) in a bath sonicator. After disruption was complete, the inoculator was removed from the 96 well plate and replaced with a standard lid, and the plate was placed in a shaker incubator overnight (37° C., 150 rpm) to determine biofilm viability at each dilution of DES. MSSA cells were allowed to grow overnight in the shaker incubator and viability was assessed via measurement of optical density at 600 nM using a plate reader (Synergy HT). The MBEC is defined as the lowest solution concentration of DES required to prevent bacterial growth in this plate.

TABLE 3 provides observed MBEC values of DES in a 2-hour challenge on MSSA biofilms (72 hr biofilms).

TABLE 3

| DES | MBEC (% by volume) |
| --- | --- |
| 4 | 0.625 |
| 5 | <0.313 |
| 6 | 1.25 |
| 7 | 10 |
| 8 | 0.625 |
| 9 | 1.25 |
| 10 | 1.25 |
| 11 | >10 |
| 12 | 10 |
| 13 | 0.625 |
| 14 | 1.25 |
| 15 | 2.5 |
| 16 | >10 |
| 17 | 0.625 |
| 18 | >10 |
| 19 | 5 |
| 1; CAGE (2:1) | 0.625 |
| 2; CAGE (1:1) | 5-10 |

Presentations of general interest relating to ionic liquids and eutectic solvents include "Interaction of Ionic Liquids with Living Systems: From Antibacterial agents to renewable Energy" by Koppisch, A., Department of Chemistry, Northern Arizona University, Sep. 16, 2016. Publications of general interest relating to ionic liquids and eutectic solvents include US Pat. Publ. US2016263225; PCT Intl. Publ. No. WO2016108083; PCT Intl. Publ. No. WO2011056545; Lovejoy, K., Lou, A., Davis, L., Sanchez, T., Iyer, S., Corley, K., Wilkes, J., Feller, R., Fox, D., Koppisch, A., Del Sesto, R. *Analytical Chem.* 2012, 84, 9169-9175; Palmer, M., Costerton, W., Sewecke, J., Altman, D. Molecular techniques to detect biofilm bacteria in long bone nonunion: a case report. *Clin Orthop Relat Res* 2011, 469 (11), 3037-3042; Zameer, F., Gopal, R. Evaluation of Antibiotic Susceptibility in Mixed Culture Biofilms. *Int J Biotechnol Biochem* 2010, 6 (1), 93-99, Fleming, H. and Wingender, J. *Nature Rev Microbiol,* 2010, 8, 623; Christensen, G. D., W.

A. Simpson, J. J. Younger, L. M. Baddour, F. F. Barrett, D. M. Melton, and E. H. Beachey. 1985. Adherence of coagulase-negative staphylococci to plastic tissue culture plates: a quantitative model for the adherence of staphylococci to medical devices. *J. Clin. Microbiol.* 22: 996-1006; O'Toole, G. A., and R. Kolter. 1998. The initiation of biofilm formation in *Pseudomonas fluorescens* WCS365 proceeds via multiple, convergent signaling pathways: a genetic analysis. *Mol. Microbiol.* 28: 449-461; D. A. Case, J. T. Berryman, R. M. Betz, D. S. Cerutti, T. E. Cheatham, III, T. A. Darden, R. E. Duke, T. J. Giese, H. Gohlke, A. W. Goetz, N. Homeyer, S. Izadi, P. Janowski, J. Kaus, A. Kovalenko, T. S. Lee, S. LeGrand, P. Li, T. Luchko, R. Luo, B. Madej, K. M. Merz, G. Monard, P. Needham, H. Nguyen, H. T. Nguyen, I. Omelyan, A. Onufriev, D. R. Roe, A. Roitberg, R. Salomon-Ferrer, C. L. Simmerling, W. Smith, J. Swails, R. C. Walker, J. Wang, R. M. Wolf, X. Wu, D. M. York and P. A. Kollman. Amber; University of California, San Francisco, 2015; Lee, J., Cheng, X., Swails, J. M., Yeom, M. S., Eastman, P. K., Lemkul, J. A., Wei, S., Buckner, J., Jeong, J. C., Qi, Y., et al. CHARMM-GUI Input Generator for NAMD, GROMACS, AMBER, OpenMM, and CHARMM/OpenMM Simulations Using the CHARMM36 Additive Force Field. *J. Chem. Theory Comput.* 2016, 12 (1), 405-413; Martinez, L., Andrade, R., Birgin, E. G., Martinez, J. M. PACKMOL: a package for building initial configurations for molecular dynamics simulations. *J. Comput. Chem.* 2009, 30 (13), 2157-2164; Dickson, C. J., Madej, B. D., Skjevik, Å. A., Betz, R. M., Teigen, K., Gould, I. R., Walker, R. C. Lipid14: The Amber Lipid Force Field. *J. Chem. Theory Comput.* 2014, 10 (2), 865-879; Jorgensen, W. L., Chandrasekhar, J., Madura, J. D., Impey, R. W., Klein, M. L. Comparison of simple potential functions for simulating liquid water. *J. Chem. Phys.* 1983, 79 (2), 926-935; Wang, J., Wolf, R. M., Caldwell, J. W., Kollman, P. A., Case, D. A. Development and testing of a general amber force field. *J. Comput. Chem.* 2004, 25 (9), 1157-1174, Sprenger, K. G., Jaeger, V. W., Pfaendtner, J. The general AMBER force field (GAFF) can accurately predict thermodynamic and transport properties of many ionic liquids. *J. Phys. Chem. B* 2015, 119 (18), 5882-5895; Skjevik, A. A., Madej, B. D., Dickson, C. J., Teigen, K., Walker, R. C., Gould, I. R. All-atom lipid bilayer self-assembly with the AMBER and CHARMM lipid force fields. *Chem. Commun.* 2015, 51 (21), 4402-4405; Madej, B. D., Gould, I. R., Walker, R. C. A Parameterization of Cholesterol for Mixed Lipid Bilayer Simulation within the Amber Lipid14 Force Field. *J. Phys. Chem. B* 2015, 119 (38), 12424-12435; Zhao, Y. H., Abraham, M. H., Zissimos, A. M. Fast Calculation of van der Waals Volume as a Sum of Atomic and Bond Contributions and Its Application to Drug Compounds. *J. Org. Chem.* 2003, 68 (19), 7368-7373; FDA, Safety and Effectiveness for Healthcare Antiseptics, (May 15, 2017); Lovejoy, K., Corley, C. A., Cope, E. K., Valentine, M. C., Leid, J. G., Purdy, G., Wilkes, J. S., Koppisch, A. T., Del Sesto, R. E.: Utilization of Metal Halide Species Ambiguity to Develop Amorphous, Stabilized, Pharmaceutical Agents as Ionic Liquids. *ACS Crystal Growth Des,* 2012, 12, 5357-5364; Lovejoy, M, Lovejoy, K, Kern, T, Miller, T, Le, V, Nagy, A, Goumas, A, Iyer, R, Del Sesto, R, Koppisch, A, Fox, D, Mitragotri, S. Ionic liquids as a class of materials for transdermal delivery and pathogen neutralization. *PNAS.* 2014, 111, 13313-13318; Zakrewsky, M, Banerjee, A, Apte, S, Kern, T, Jones, M, Del Sesto, Koppisch, Fox, D, Mitragotri, S. Choline and Geranate Deep Eutectic Solvent as a Broad-Spectrum Antiseptic Agent for Preventive and Therapeutic Applications. *Advanced Healthcare Materials.* 2016, 5, 1282-1289; Swatloski et al, Dissolution of Cellulose with Ionic Liquids. *JACS,* 2002, 124, 4974-4975; Davies, D. Understanding Biofilm Resistance to Antibiotic Agents. *Nature Reviews Drug Discovery,* 2003, 2, 114-122; Biofilms: The Hypertextbook, 2011, 4th Ed, Cunningham, A. B., Lennox, J. E., Ross, R. J. Eds; Costerton, J., Stewart, P. S., Greenberg, E. P. Bacterial Biofilms: A Common Cause of Persistent Infections. *Science,* 1999, 284, 1318-1322, the contents of each of which is hereby incorporated by reference in its entirety.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An ionic liquid matrix comprising:
   a neutral species;
   an isoprenoid anion; and
   a cholinium cation,
   wherein the neutral species, the isoprenoid anion, and the cholinium cation are present in a molar ratio of 1:1:1, and
   wherein the neutral species is selected from the group consisting of carvacrol, citronellic acid and farnesol.

2. The ionic liquid matrix of claim 1, wherein the isoprenoid anion is selected from the group consisting of geranate anion, citronellate anion, cinnamate anion, gibberelate anion, isovalerate anion, absciscate anion, indole-3-butyrate anion, salicylate anion, protocatechuate anion and abietate anion.

3. An antibiofilm material, comprising
   the iconic liquid matrix of claim 1; and
   a solvent.

4. The antibiofilm material of claim 3, wherein the ionic liquid matrix is present in the antibiofilm material at a concentration of from 0.01% by volume to 20% by volume.

5. The antibiofilm material of claim 3, wherein the ionic liquid matrix is present in the antibiofilm material at a concentration of from 0.1% by volume to 15% by volume.

6. The antibiofilm material of claim 3, wherein the ionic liquid matrix is present in the antibiofilm material at a concentration of from 1% by volume to 10% by volume.

7. The antibiofilm material of claim 3, further comprising a compound exhibiting stabilizing or preservative activity.

8. The antibiofilm material of claim 4, wherein the compound exhibiting stabilizing or preservative activity is selected from the group consisting of α-tocopherol, α-tocopherol acetate, β-carotene, lutein, salicylic acid, protocatechuic acid.

9. The antibiofilm material of claim 7, wherein the compound exhibiting stabilizing or preservative activity is present at a concentration of 0.1% by volume to 5% by volume.

10. The antibiofilm material of claim 7, wherein the compound exhibiting stabilizing or preservative activity is present at a concentration of 1% by volume to 2% by volume.

11. A method of killing a bacterium, comprising:
contacting a bacterium with the antibiofilm material of claim 3, whereby the bacterium is killed.

12. The method of claim 11, wherein the bacterium is selected from the group consisting of *Staphylococcus aureus, Pseudomonas aeruginosa, Enterobacter cloacae, Enterococcus* sp., and *Escherichia coli, Acinetobacter baumani*, and *Klebsiella pneumoniae*.

13. A cleaning solution comprising the antibiofilm material of claim 3.

14. A delivery vehicle for an antibiofilm drug comprising the antibiofilm material of claim 3.

15. The ionic liquid matrix of claim 1, wherein the neutral species is carvacrol.

16. The ionic liquid matrix of claim 1, wherein the neutral species is citronellic acid.

17. The ionic liquid matrix of claim 1, wherein the neutral species is farnesol.

\* \* \* \* \*